(12) United States Patent
Schirhagl et al.

(10) Patent No.: US 9,557,250 B2
(45) Date of Patent: Jan. 31, 2017

(54) DEVICES AND METHODS FOR SEPARATING PARTICLES

(71) Applicant: The Board of Trustees of the Leland Stanford Junior University, Palo Alto, CA (US)

(72) Inventors: Romana Schirhagl, Steyr (AT); Richard N. Zare, Stanford, CA (US); Kangning Ren, Palo Alto, CA (US); Niaz Banaei, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 351 days.

(21) Appl. No.: 13/787,874

(22) Filed: Mar. 7, 2013

(65) Prior Publication Data
US 2013/0309657 A1    Nov. 21, 2013

Related U.S. Application Data

(60) Provisional application No. 61/648,223, filed on May 17, 2012, provisional application No. 61/700,929, filed on Sep. 14, 2012.

(51) Int. Cl.
*B01J 20/281*      (2006.01)
*G01N 1/34*       (2006.01)
(Continued)

(52) U.S. Cl.
CPC ............... *G01N 1/34* (2013.01); *B01J 20/268* (2013.01); *B01J 20/3057* (2013.01); *B01L 3/502707* (2013.01); *B01L 3/502761* (2013.01); *B29C 59/005* (2013.01); *G01N 1/405* (2013.01); *B01L 2200/0668* (2013.01); *B01L 2300/0636* (2013.01); *B01L 2300/0816* (2013.01); *B01L 2400/0409* (2013.01)

(58) Field of Classification Search
CPC ..... B01J 20/268; B01J 20/305; B01J 20/3057; B01J 2219/0063; B01J 2219/00659; B01J 2219/00382; G01N 2600/00; G01N 2650/00; G01N 33/543; G01N 1/34; G01N 1/405; G01N 21/07; G01N 35/00069; C07K 17/08; B29C 59/00; B29C 59/005; B29C 39/00; B29C 39/003; B29C 39/006; B29C 39/02; B82Y 30/00; B82Y 40/00; B82Y 5/00; B82Y 15/00; B01D 21/262; B01D 2221/10; B01L 2400/0409; B01L 2300/0803; B01L 2300/0851; B01L 2300/165; B01L 3/5027; B01L 3/50273
USPC ....... 435/287.1; 436/12, 177, 524, 528, 531; 422/64, 68.1, 72, 504, 551
See application file for complete search history.

(56) References Cited

U.S. PATENT DOCUMENTS 8,287,908 B2    10/2012   Kristensen
8,377,717 B2    2/2013    Bright
(Continued)

FOREIGN PATENT DOCUMENTS

FR    WO 2010026308 A1 *    3/2010    ............ B01J 20/26
WO         2012031128 A3         8/2012

*Primary Examiner* — Erik B Crawford
(74) *Attorney, Agent, or Firm* — Thomas | Horstemeyer, LLP

(57) ABSTRACT

Embodiments of the present disclosure provide for particle-imprinted polymer films, methods of making particle-imprinted polymer films, methods for separating particles, devices or systems for separating particles, and the like.

5 Claims, 17 Drawing Sheets

(51) Int. Cl.

| | |
|---|---|
| *B29C 59/00* | (2006.01) |
| *B01J 20/26* | (2006.01) |
| *B01J 20/30* | (2006.01) |
| *G01N 1/40* | (2006.01) |
| *B01L 3/00* | (2006.01) |

(56) References Cited

U.S. PATENT DOCUMENTS

| | | | |
|---|---|---|---|
| 2003/0219828 A1* | 11/2003 | Singh et al. | 435/7.1 |
| 2004/0058380 A1 | 3/2004 | Levon et al. | |
| 2007/0039835 A1* | 2/2007 | Rossier et al. | 205/792 |
| 2008/0071003 A1 | 3/2008 | Sellergren et al. | |
| 2008/0152546 A1* | 6/2008 | Bedingham et al. | 422/103 |
| 2009/0325147 A1 | 12/2009 | Jones | |
| 2010/0068820 A1* | 3/2010 | Meathrel et al. | 436/95 |
| 2011/0087315 A1* | 4/2011 | Richardson-Burns et al. | 607/116 |
| 2011/0124076 A1* | 5/2011 | Ueda | C12M 47/02 435/173.9 |
| 2011/0166297 A1* | 7/2011 | Grynszpan | C08F 220/06 525/326.9 |
| 2012/0100358 A1* | 4/2012 | Haupt | B01J 20/26 428/220 |
| 2013/0137117 A1 | 5/2013 | Levi et al. | |

\* cited by examiner

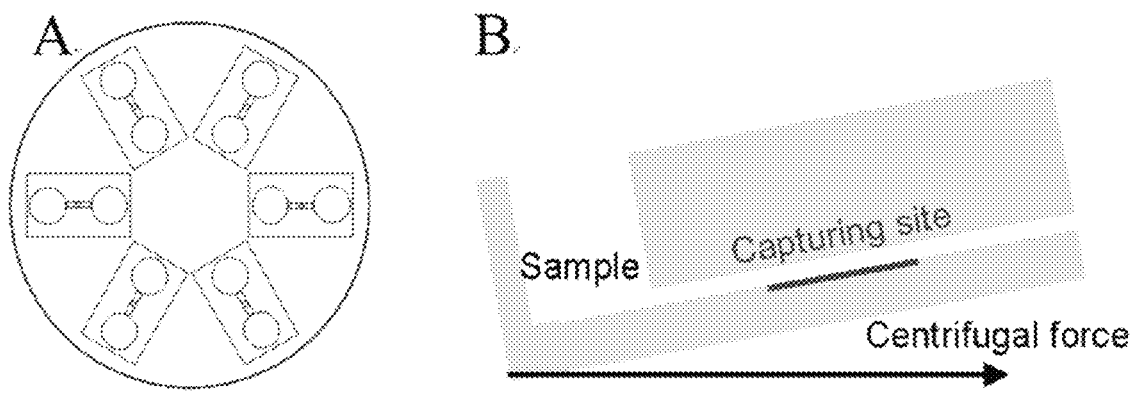
FIG. 1.1
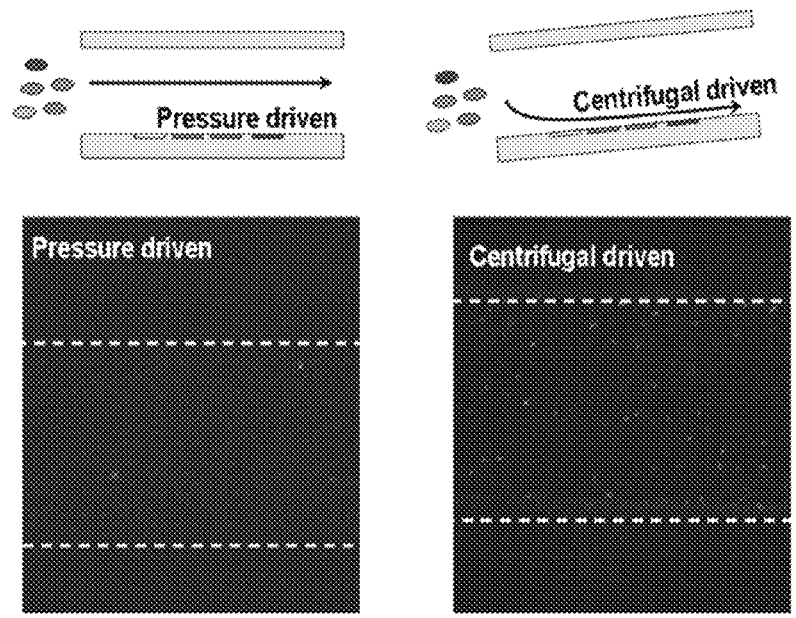
FIG. 1.2

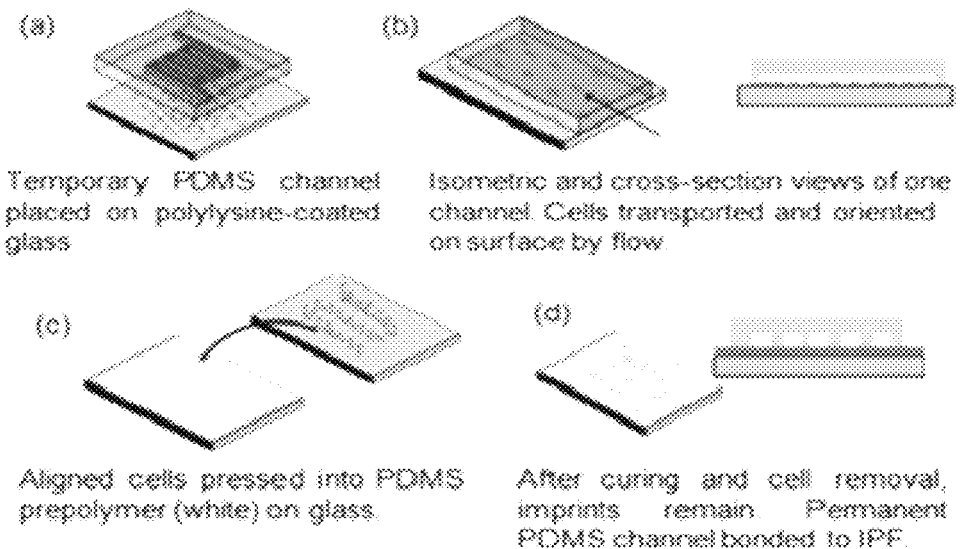
FIG. 2.1
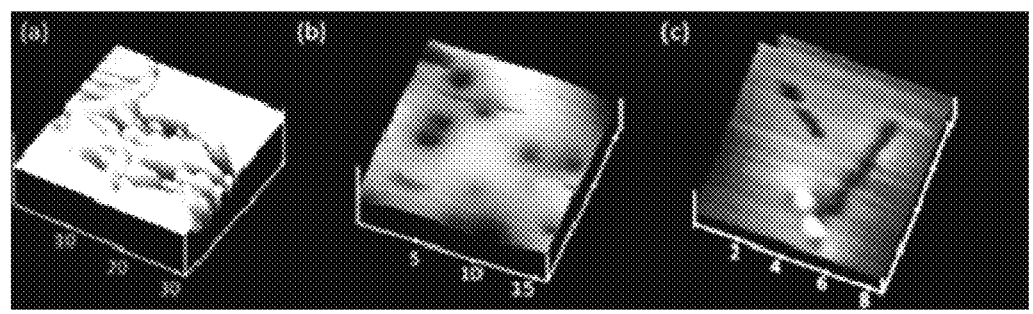
FIG. 2.2

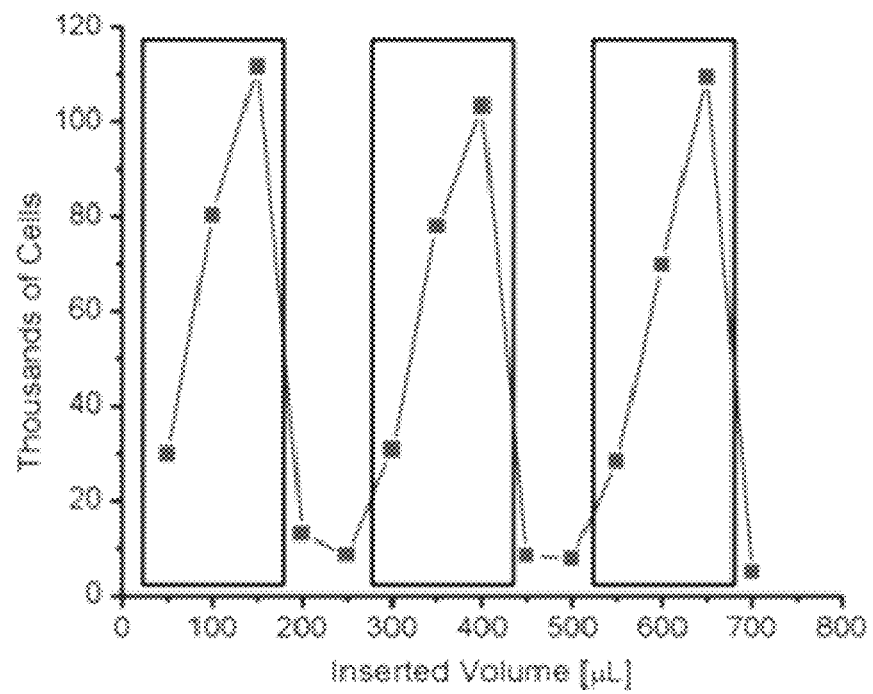
FIG. 2.3
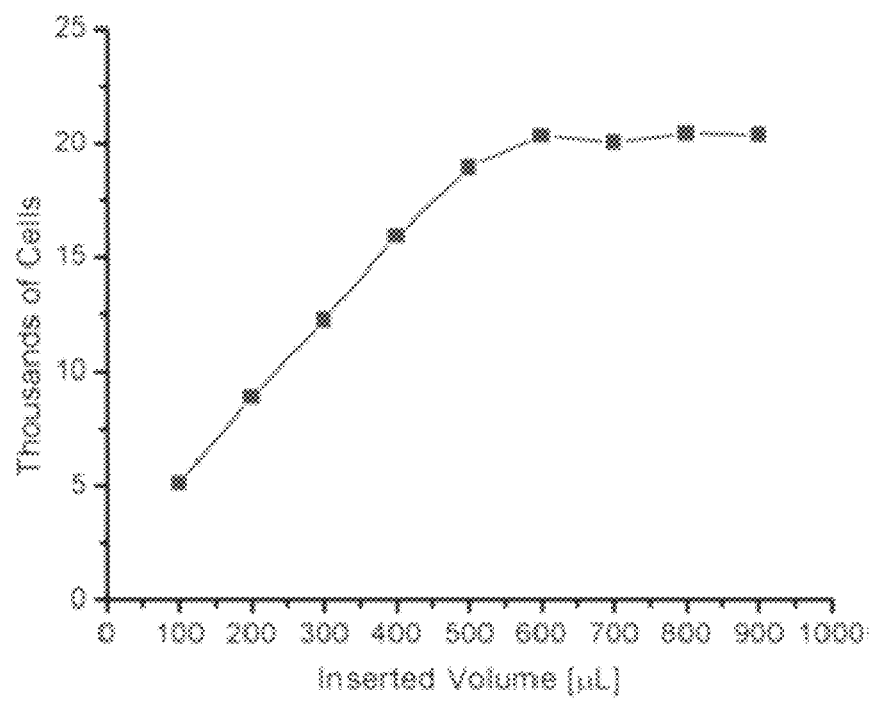
FIG. 2.4

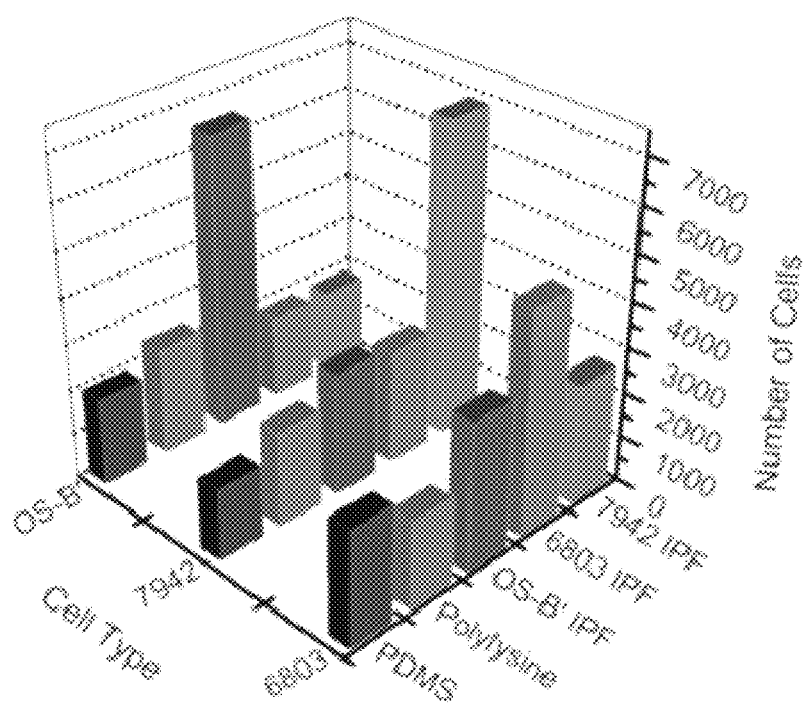
FIG. 2.5

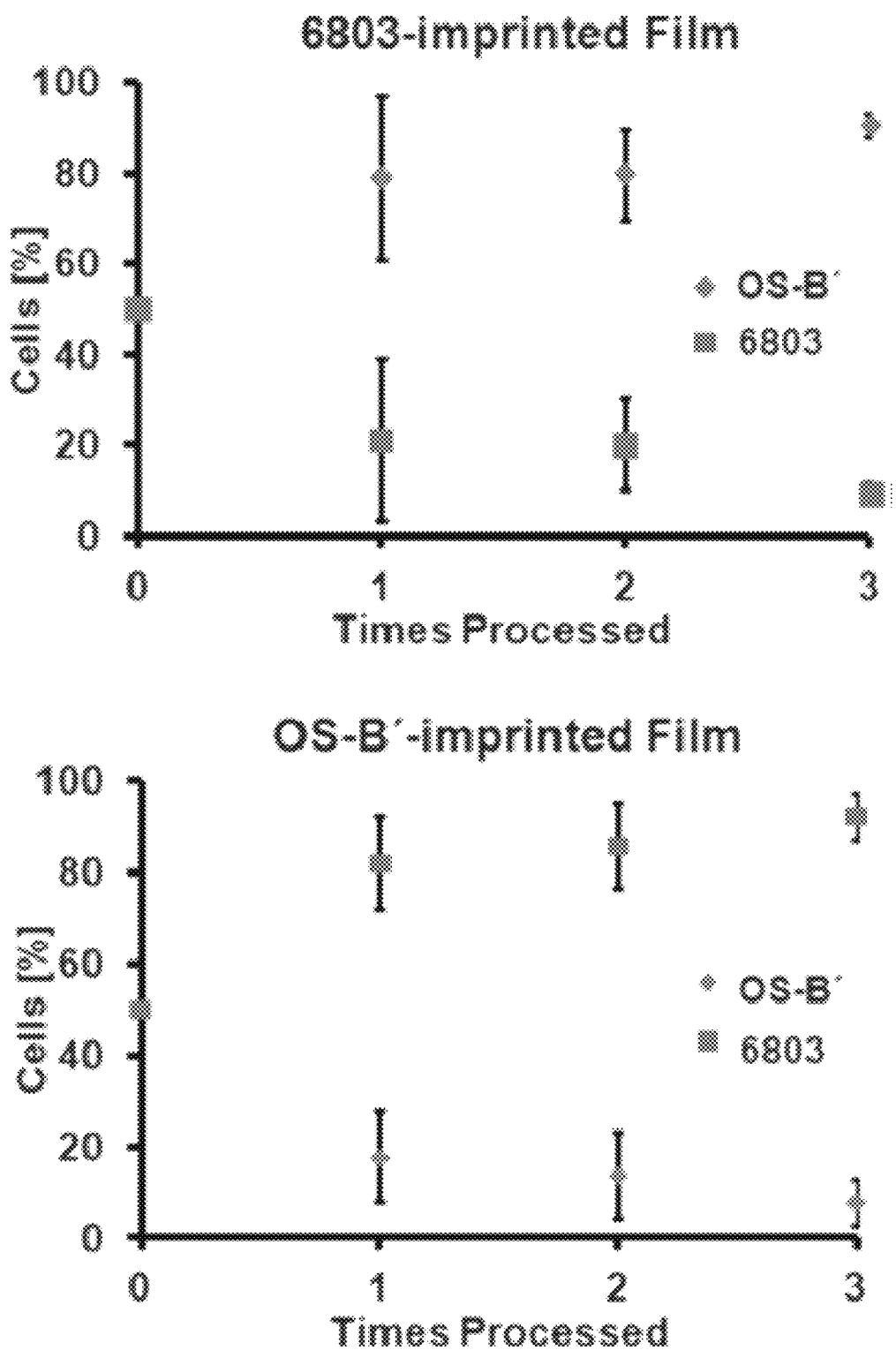
FIG. 2.6

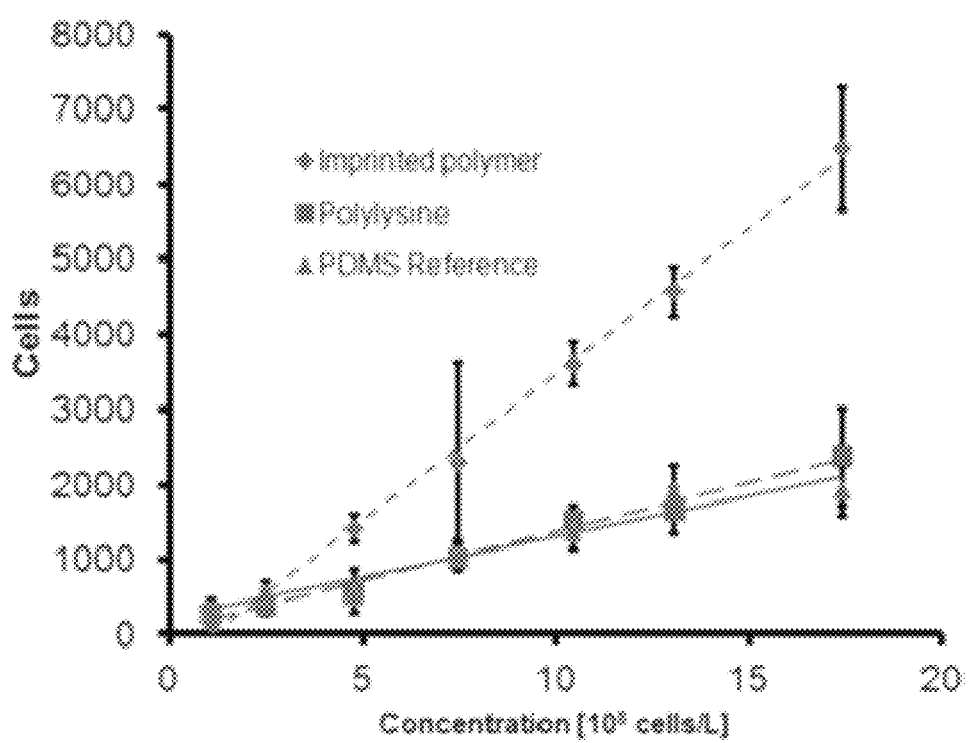
FIG. 2.7

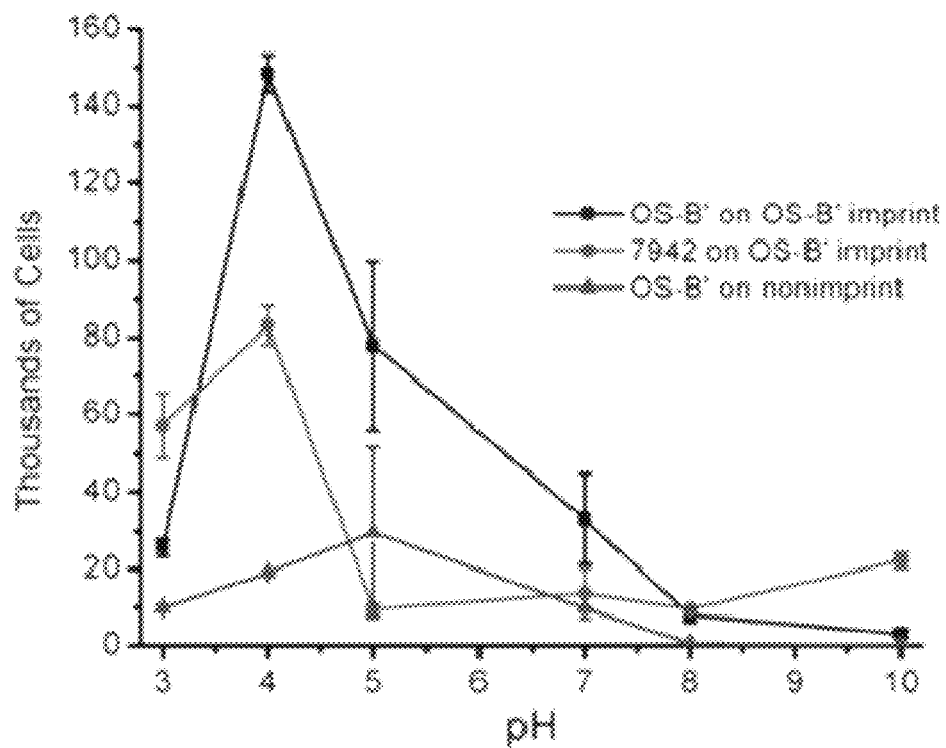
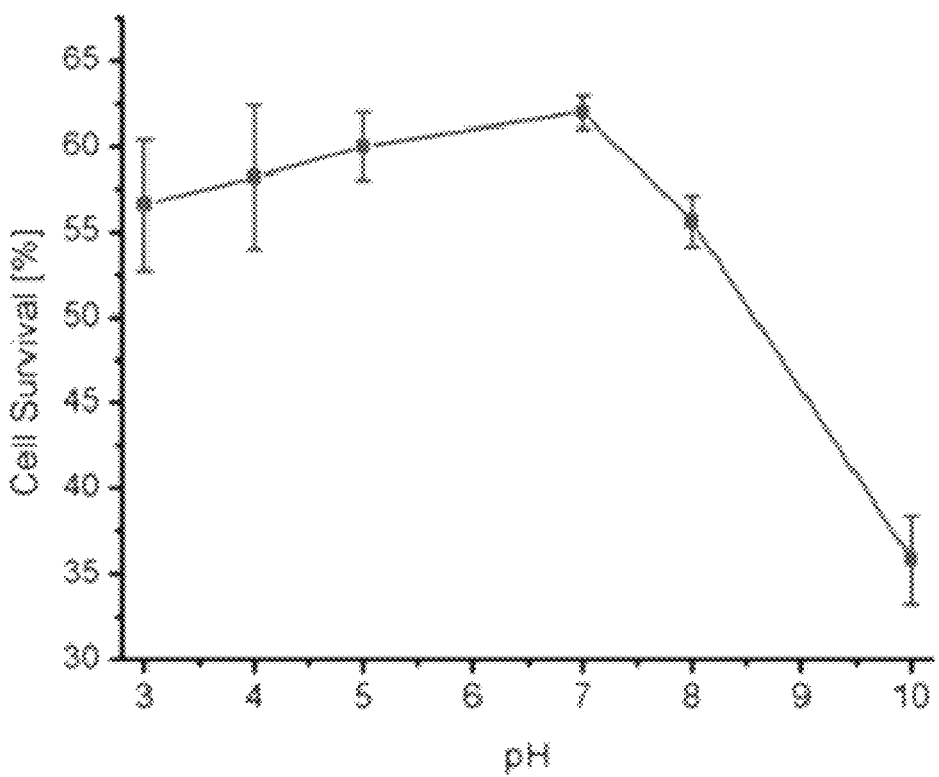
FIG. 2.8

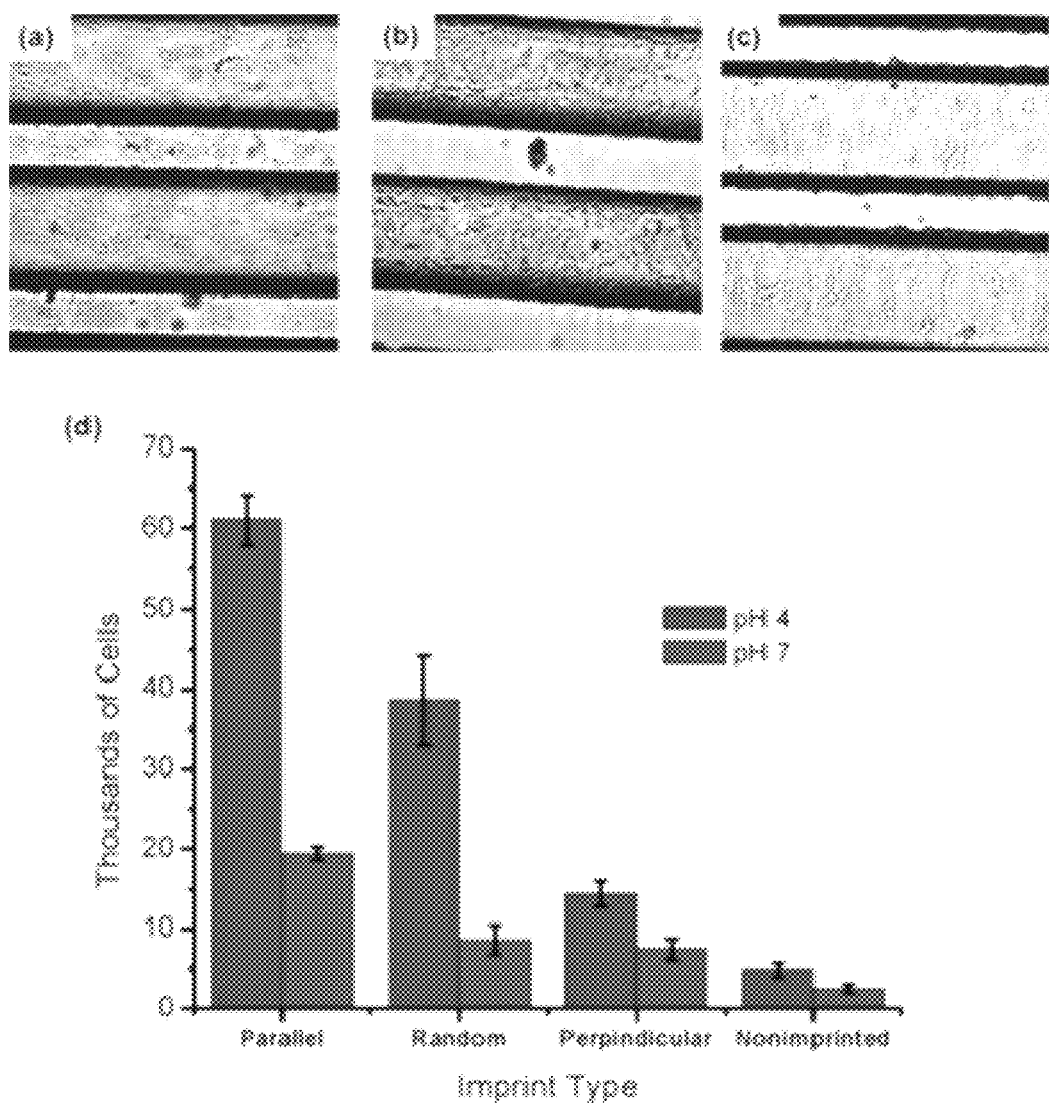
FIG. 2.9

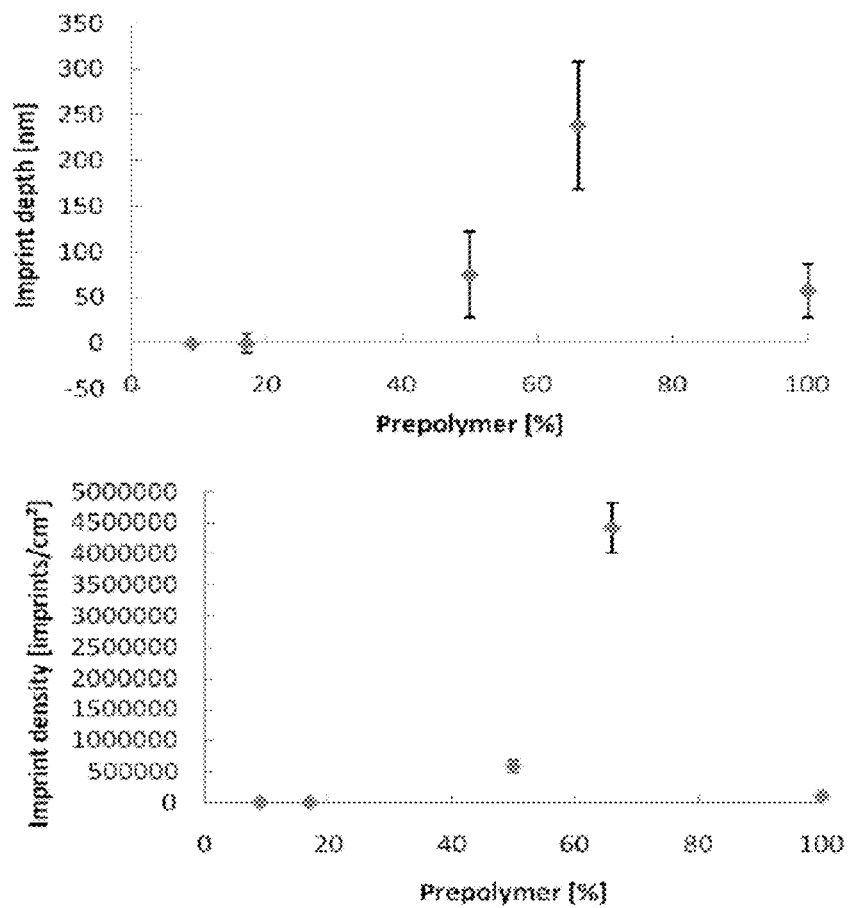
FIG. 2.10
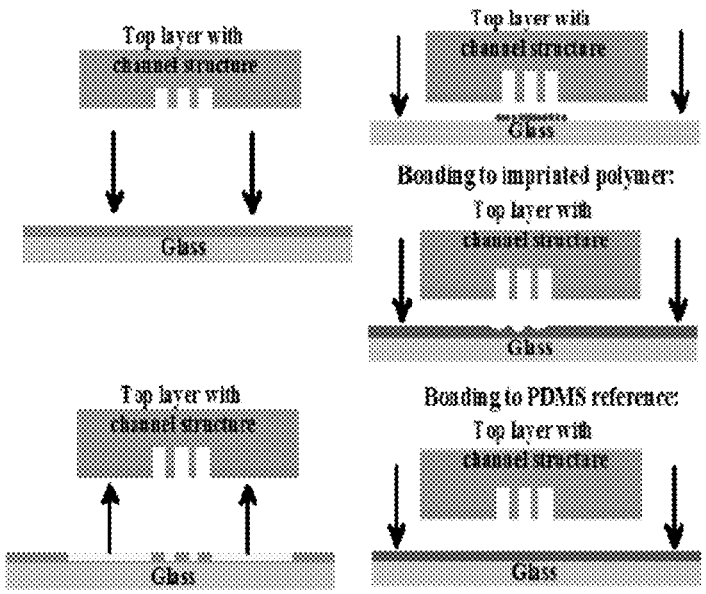
FIG. 2.11

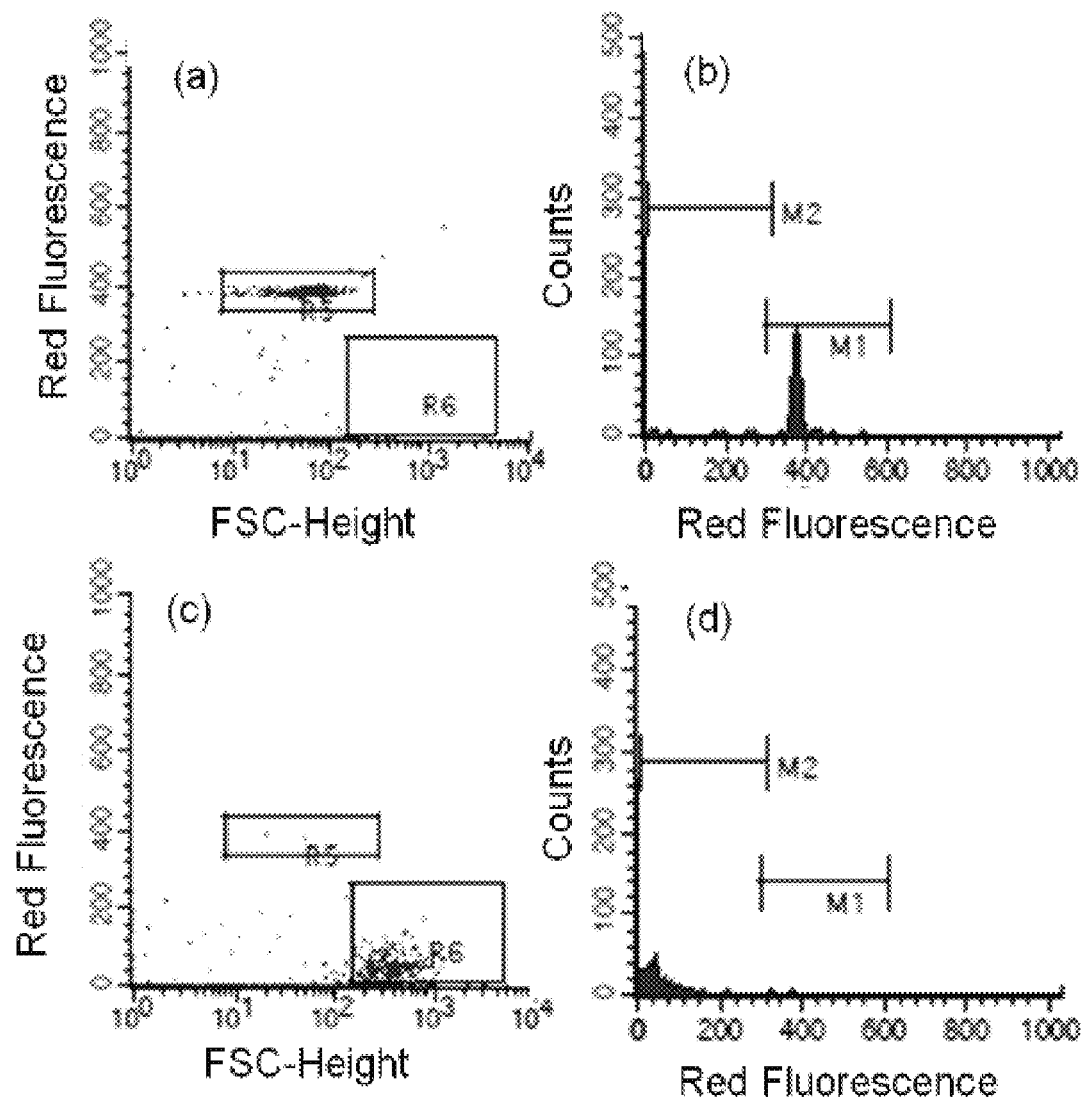
FIG. 2.12

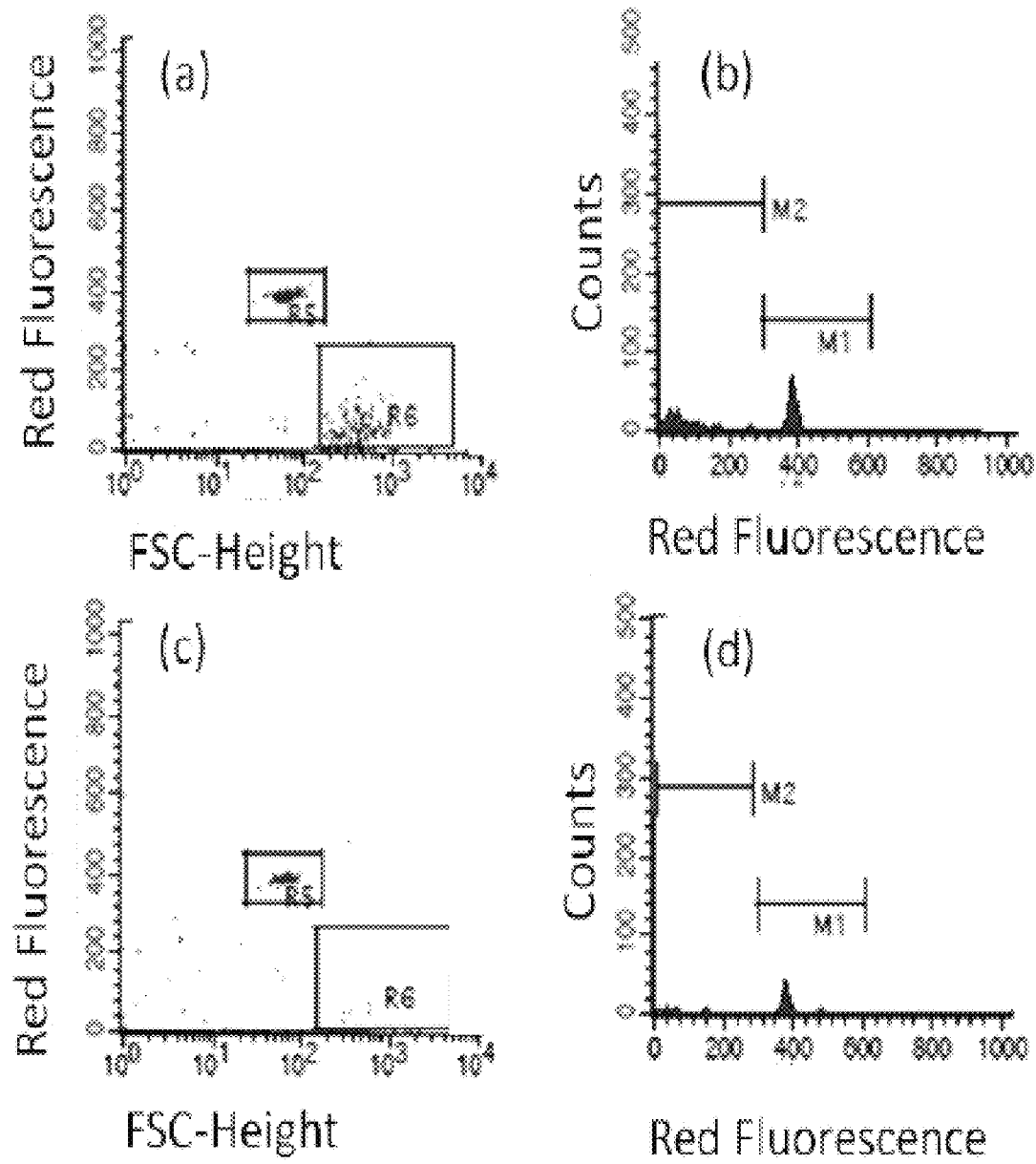
FIG. 2.13

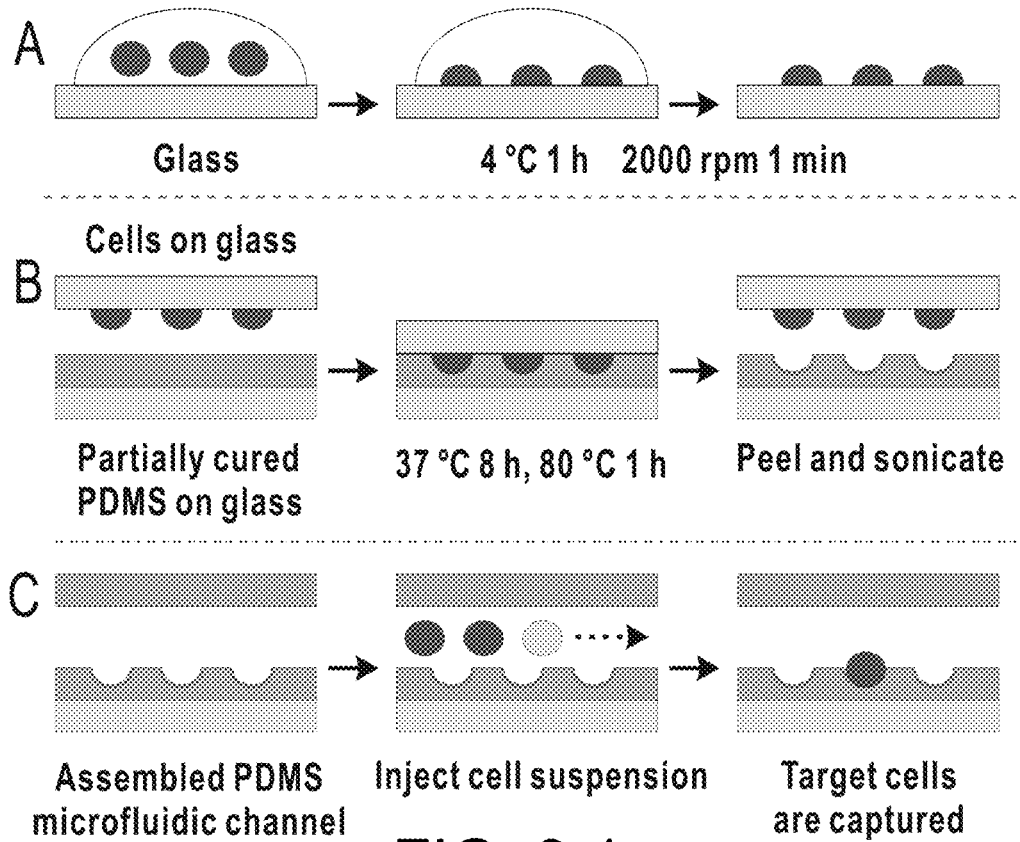
FIG. 3.1
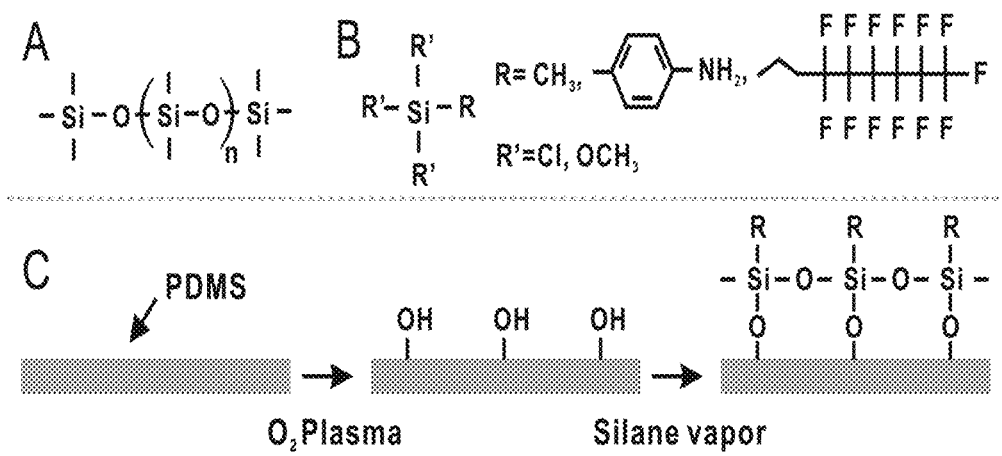
FIG. 3.2

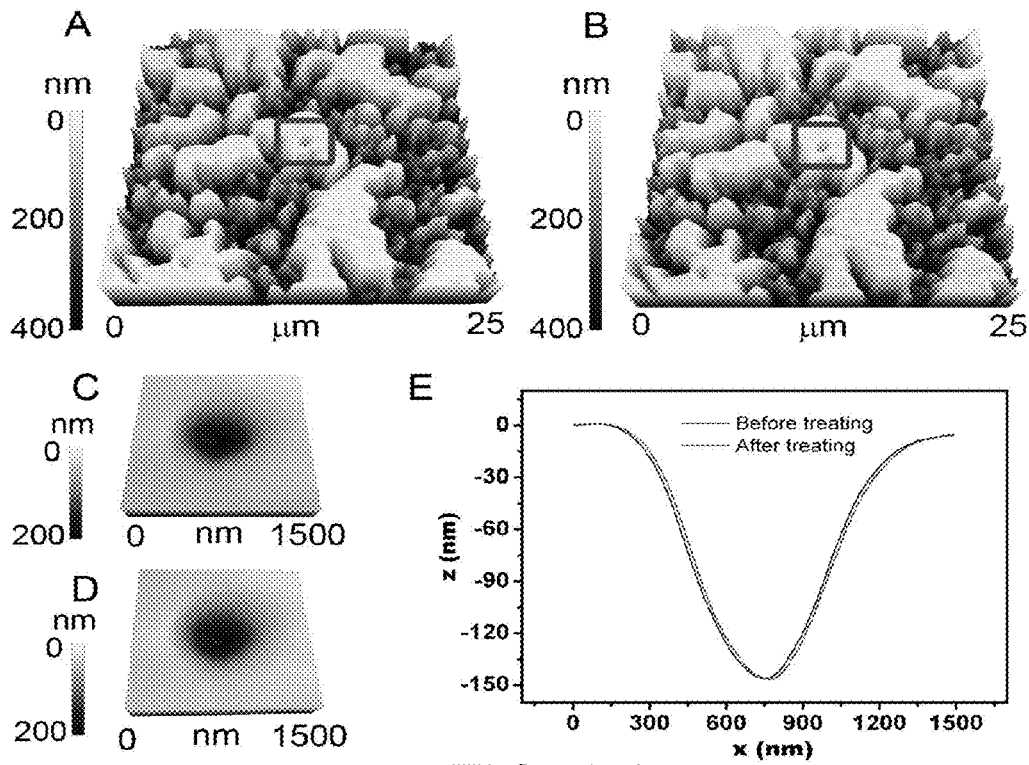
FIG. 3.3
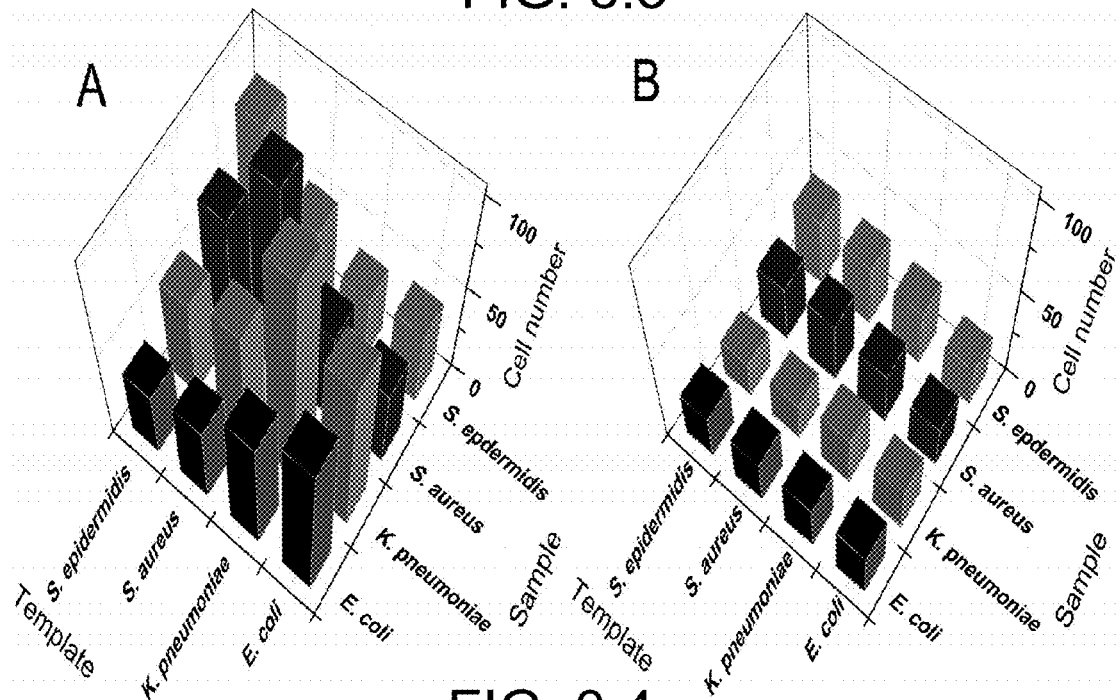
FIG. 3.4

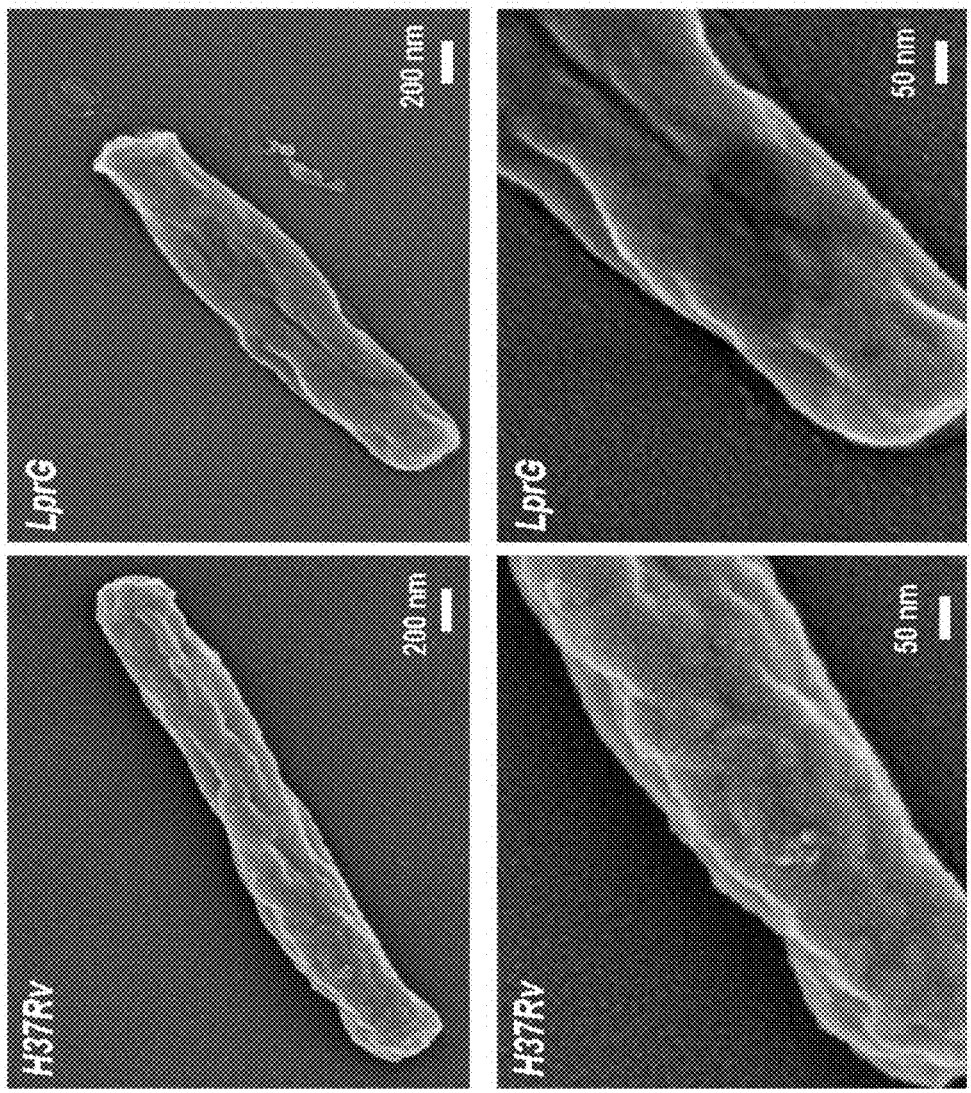
FIG. 4.1

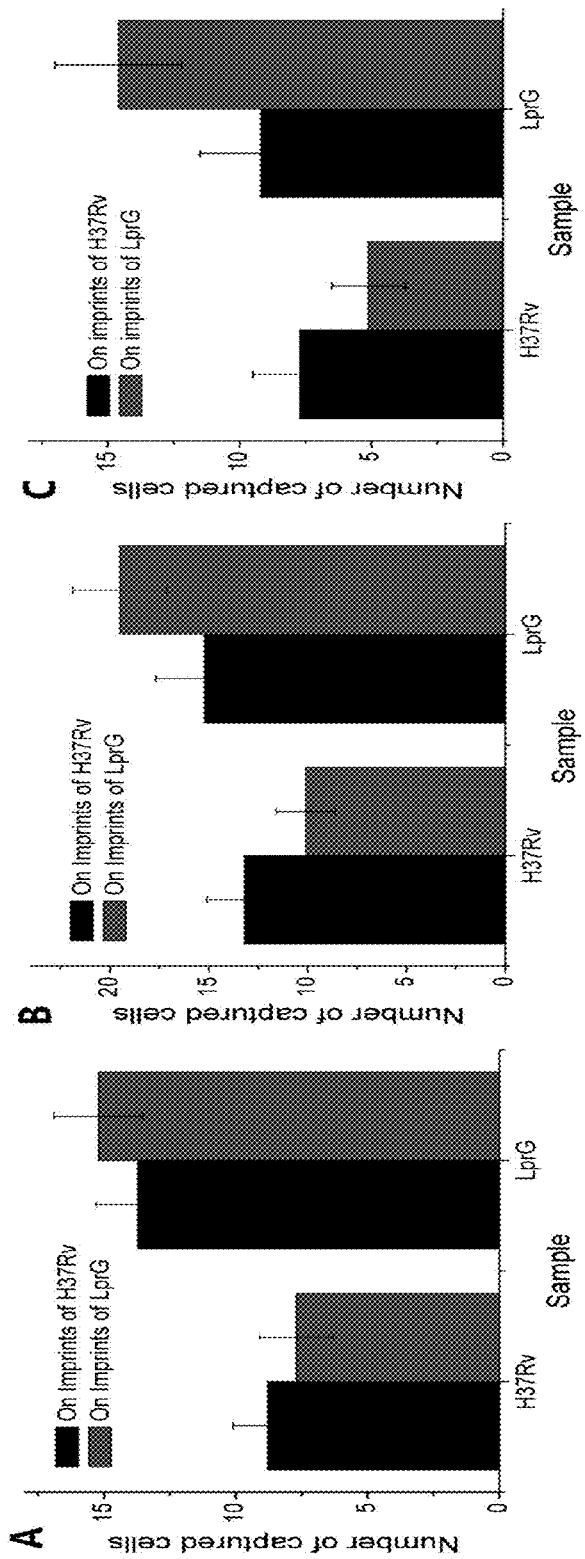
FIG. 4.2
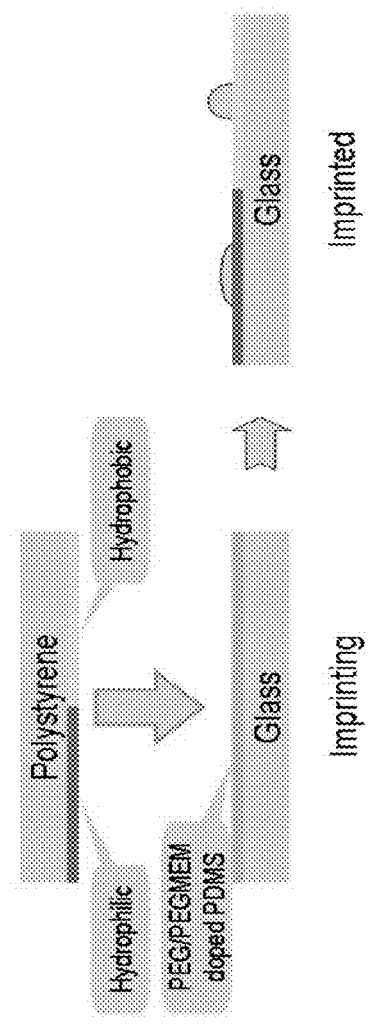
FIG. 5.1

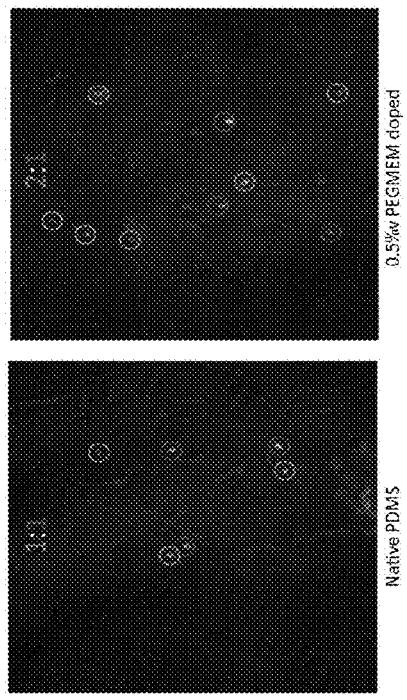
FIG. 6.1
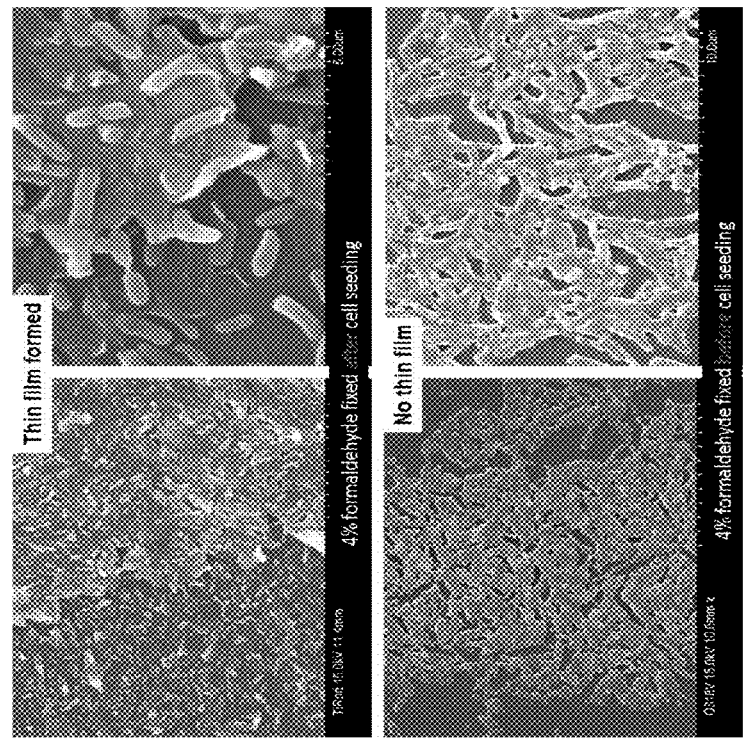
FIG. 7.1

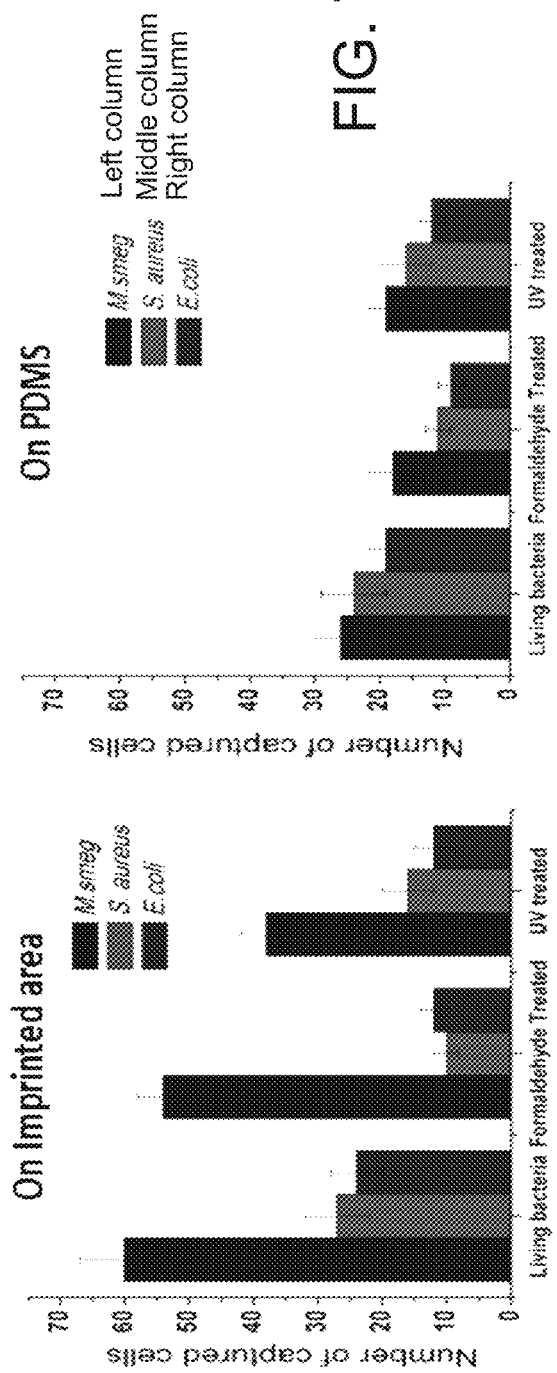
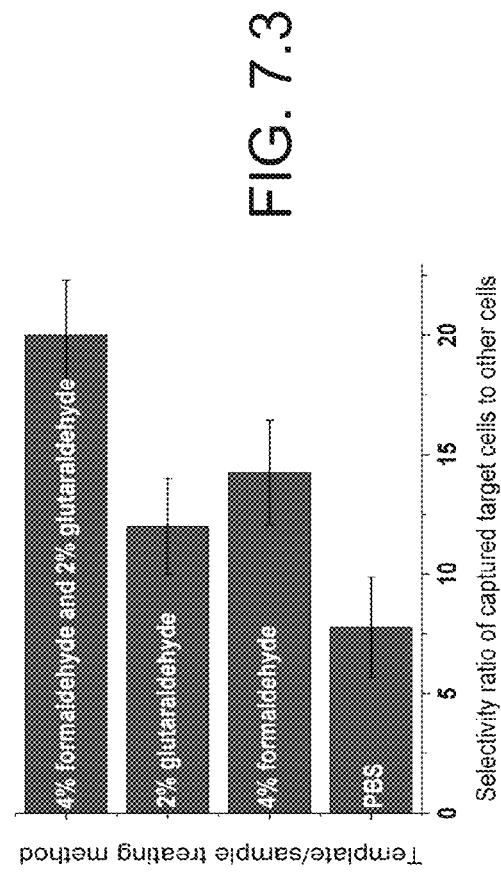
FIG. 7.2
FIG. 7.3

DEVICES AND METHODS FOR SEPARATING PARTICLES

CLAIM OF PRIORITY TO RELATED APPLICATION

This application claims priority to U.S. provisional application entitled "DEVICES AND METHODS FOR SEPARATING PARTICLES" having Ser. No. 61/648,223 filed on May 17, 2012, which is entirely incorporated herein by reference. This application also claims priority to U.S. provisional application entitled "DEVICES AND METHODS FOR SEPARATING PARTICLES" having Ser. No. 61/700,929, filed on Sep. 14, 2012, which is entirely incorporated herein by reference.

FEDERAL SPONSORSHIP

This invention was made with Government support under contracts MCB0749638 awarded by the National Science Foundation, and TW008781 awarded by the National Institutes of Health. The Government has certain rights in this invention.

BACKGROUND

Separation is a key issue in many fields and applications, including analytical chemistry, diagnostics, environmental science, and synthesis and purification. In contrast to separations of small molecules, which can be performed reliably via chromatography, cell separations are still challenging. Filter-based and magnetic separations are the methods of choice to handle multiple cells simultaneously; however, they require that cells possess a significant size difference or be magnetically labeled. Thus, there is a need to using alternative methods of separating cells.

SUMMARY

In accordance with the purpose(s) of the present disclosure, as embodied and broadly described herein, embodiments of the present disclosure provide for particle-imprinted polymer films, methods of making particle-imprinted polymer films, methods for separating particles, devices or systems for separating particles, and the like.

In an embodiment, the method of making a particle-imprinted polymer film includes: disposing at least one type of target particle onto a first substrate, wherein the target particles are attached to the first substrate, wherein the attached target particles on the first substrate form a stamp; disposing a prepolymer onto a second substrate; partially curing the prepolymer film; pressing the stamp into the partially cured prepolymer film; curing the prepolymer film forming a particle-imprinted polymer film; and removing the stamp and removing any particle residue from the particle-imprinted polymer film.

In an embodiment, the method of separating particles includes: exposing a particle-imprinted polymer film comprising indentations to a sample comprising at least one target particle, wherein the indentations preferentially capture the at least one target particle in the sample; and removing material not captured from the particle-imprinted polymer film.

In an embodiment, the particle-imprinted polymer film includes: a polymer film having indentations that have non-covalent chemical binding characteristics that preferentially capture at least one type of target particle.

In an embodiment, the microfluid device includes: a particle-imprinted polymer film having a polymer film having indentations that have non-covalent chemical binding characteristics that preferentially capture at least one type of target particle.

In an embodiment, the microfluidic device for separating target particles includes: a sample holding area; a second area including one or more particle-imprinted polymer films having a polymer film having indentations that have non-covalent chemical binding characteristics that preferentially capture at least one type of target particle, wherein the second area is in fluidic communication with the sample holding area via one or more inlets; and a structure that is used to generate a centrifugal force, wherein the sample holding area and the second area are disposed on or are part of the structure, wherein each particle-imprinted polymer film is disposed on a substrate that is in a plane that is at an angle to the plane of the centrifugal force, wherein the centrifugal force causes the sample to move from the sample holding area into the second area.

Other systems, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 is a schematic of a device on the turntable, with a dip or incline angle (e.g., about 1 to 45 degrees) with the turntable plane and includes an embodiment of the particle-imprinted polymer film.

FIG. 1.2 illustrates an image showing the difference of captured cells using a pressure driven approach and a centrifugal driven approach.

FIG. 2.1 is a schematic of a fabrication scheme for oriented IPF microdevice. FIG. 2.1(a) illustrates a temporary PDMS structure placed on polylysine-coated glass. FIG. 2.1(b) illustrates a cell suspension is moved through the channel using negative pressure, oriented by flow. FIG. 2.1(c) illustrates the top layer is removed and the glass plate with oriented cells is used for imprinting. FIG. 2.1(d) illustrates oriented imprints remain when the cells are removed. Cross-section shows the final chip after bonding of permanent structure (100 mm channels).

FIG. 2.2 illustrates AFM images of imprinted PDMS surfaces following cell removal: FIG. 2.2(a), *Synechococcus* OS-B0, FIG. 2.2(b), *Synechocystis* PCC 6803, and FIG. 2.2(c), *Synechococcus* elongates PCC 7942.

FIG. 2.3 illustrates the reversibility of Syn OS-B0 capture. When a cell suspension is injected, cells are accumulated on the surface (black frames). After each accumulation, the chip was washed with 0.01% polylysine in water.

FIG. 2.4 illustrates accumulation of Syn OS-B0 cells on an imprinted surface.

FIG. 2.5 is a graph that illustrates selectivities of different coatings (y-axis) exposed to the same concentration of respective bacterial species (x-axis).

FIG. 2.6 illustrates graphs of 1:1 mixtures of two cyanobacterial strains (Syn OS-B0 and 6803) were processed sequentially through separate devices of two types: 6803-imprinted (top) and Syn OS-B0-imprinted (bottom). Flow cytometry data was taken of each suspension after processing through each device.

FIG. 2.7 illustrates sensor responses of Syn OS-B0-imprinted PDMS, polylysine, and bare PDMS to a range of Syn OS-B0 concentrations.

FIG. 2.8 is a graph that illustrates the adhesion of Syn OS-B0 and Syn 7942 to Syn OS-B0-imprinted surfaces and a non-imprinted reference at different pH values was measured (top). Additionally, viability of Syn OS-B0 under the same range of pH values was also studied. The viability of an untreated reference was 63.4%. Error bars were determined from three experiments using different chips.

FIG. 2.9 illustrates a comparison of imprints oriented: FIG. 2.9(a) parallel to the flow, FIG. 2.9(b) at random, and FIG. 2.9(c) perpendicular to the flow. Capture efficiency of each imprint type, as well as a non-imprinted reference, to Syn OS-B0 was tested at pH 4 and pH 7 FIG. 2.9(d).

FIG. 2.10 is a graph showing the optimization of the imprinted polymer. The polymer was optimized to obtain the maximum imprint depth that is possible where the cells can still be removed after imprinting. (For some points, the error bars are smaller than the data point.)

FIG. 2.11 is a schematic that shows the mortar-based binding of the top layer to the capturing surface in more detail.

FIG. 2.12 illustrates graphs of flow cytometry data for the pure components. Pure labeled beads (FIG. 2.12a, b) and pure bacteria (FIG. 2.12c, d) were measured separately. Particles showing up in areas R5 and M1 were identified as beads and particles in R6 and M2 as cells.

FIG. 2.13 illustrates graphs showing flow cytometry data taken before (FIG. 2.13a, b) and after (FIG. 2.13c, d) adhesion-based separation of a mixture of cyanobacteria and fluorescent beads with a cyanobacteria-imprinted polymer. The relative abundance of cyanobacteria significantly decreases (R6 and M2) whereas the relative abundance of labeled beads (R5 and M1) increases.

FIG. 3.1 illustrates a schematic diagram of the cell imprinting process and its application for cell sorting: FIG. 3.1(A), preparation of the template; FIG. 3.1(B), polymer imprinting with the cell template; and FIG. 3.1(C), cell sorting with the CIP microfluidic chip.

FIG. 3.2 illustrates schemes of chemical structure of: FIG. 3.2(A) PDMS, FIG. 3.2(B) Silanes used for treating the CIP chip, and FIG. 3.2(C), the silanization process of the CIP chip.

FIG. 3.3 illustrates AFM images of a same location on the PDMS surface containing imprints of *Staphylococcus aureus*: FIG. 3.3(A), before silanization, and FIG. 3.3(B) after silanization. Close-ups of the areas marked with red squares in FIG. 3.3(A) and FIG. 3.3(B) are shown in FIG. 3.3(C) and FIG. 3.3(D) and the profiles of these areas are presented in FIG. 3.3(E).

FIG. 3.4 illustrates the numbers of different cells captured on CIPs imprinted by different bacteria for FIG. 3.4(A) unmodified CIPs and FIG. 3.4(B) the corresponding silanized CIPs.

FIG. 4.1 illustrates SEM images of MTB H37Rv and MTB ΔLprG.

FIG. 4.2 illustrates the number of cells captured on cell-imprinted area of polymer surfaces. (A) PDMS, (B) PDMS doped with 0.1% PDADMAC and (C) PDMS doped with 0.5% PEGMEM.

FIG. 5.1 illustrates imprints of the stability test using water contact angle measurement.

FIG. 6.1 illustrates examples of cell capturing results on cell imprints with low occupancy of the surface.

FIG. 7.1 illustrates SEM images of cell-imprinting templates made with living and inactivated bacteria. *M. smeg* suspension in PBS was used for seeding the cells to the substrate. After sedimentation of the cells at 4° C. overnight the buffer was removed by centrifugation.

FIG. 7.2 illustrates a comparison of cell capturing performance on imprinted PDMS and on native PDMS. Living bacteria and bacteria inactivated by UV or 4% formaldehyde were used for the tests; for each test the template and the sample were the same bacteria treated with the same method.

FIG. 7.3 illustrates the selectivity of cell capturing on cell-imprints obtained with cells treated by different inactivation methods. The selectivity is calculated by dividing the number of template cells (*M. smeg*) with the number of other cells (*E. coli*), captured on the imprints of template cell on PDMS. For each test the template and the sample were treated with the same method.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, polymer chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definition

The term "sample" can refer to a tissue sample, cell sample, a fluid sample, and the like. The sample may be taken from a host or from the environment. The tissue sample can include hair (including roots), buccal swabs, blood, saliva, semen, muscle, or from any internal organs. The fluid may be, but is not limited to, urine, sputum, blood, ascites, pleural fluid, spinal fluid, beverage, tap water, drain water, lake water, and the like. The body tissue can include, but is not limited to, skin, muscle, endometrial, uterine, and cervical tissue. In an embodiment, the cell sample can be obtained from food, living environment, public area, the field, laboratory culture, for example. In the present disclosure, the source of the sample is not critical.

The term "inactivate" can refer to causing a particle such as a cell or the like to die or be killed. In an embodiment, inactivate can refer to a particle such as a cell or the like so that is no longer infectious or dangerous to human handling the inactivated particle.

Discussion

Embodiments of the present disclosure provide for particle-imprinted polymer films, methods of making particle-imprinted polymer films, methods for separating particles, devices or systems for separating particles, and the like. In an embodiment the target particles can be active or inactivated target particles (e.g., inactivated cells). An embodiment of the present disclosure is advantageous because particles such as cells (active or inactivated) can be separated in a high-throughput fashion. Another advantage is that the separation can be conducted in a label-free manner. Another advantage is that embodiments of the present disclosure can eliminate the risk of handling infectious microorganism during the separation. Another advantage is that embodiments of the present disclosure are simpler and less expensive than other separation techniques. Another advantage is that embodiments of the present disclosure allow on-site applications without the requirement of facilities and/or power. Another advantage is that embodiments of the present disclosure permit selective separation and release of the particles separated.

In general, embodiments of the present disclosure can be used to separate one or more types of target particles (e.g., cells, bacteria, viruses, fungi, oocytes, modified cells, and the like) from a sample. In an embodiment the target particles can be active or inactivated target particles (e.g., inactivated cells). In an embodiment, the cells can be inactivated using a light source (e.g., UV light) and/or chemical processes (e.g., formaldehyde). Throughout the disclosure, reference to inactivated cells only illustrates an embodiment and other particles (e.g., active or inactivated) can be separated using embodiments of the present disclosure.

In an embodiment, a particle-imprinted polymer film can be formed so that it preferentially captures one or more inactivated target cells. The particle-imprinted polymer film includes indentations that capture one or more types of inactivated target cells, where the indentations have shapes and sizes that are similar to each type of inactivated target cell(s) and the indentations can also have non-covalent chemical binding characteristics (e.g., chemical recognition involving forces of attraction such as hydrogen bonding, hydrophobic or hydrophilic forces, van der Waals forces, electrostatic effects, and the like) that capture the cell(s). In an embodiment, the non-covalent characteristics can refer to chemical recognition that is retained by the particle-imprinted polymer film. In an embodiment, the particle-imprinted polymer film can be used to capture two or more types of inactivated target cells (e.g., two or more types of inactivated bacteria; an inactivated virus and an inactivated bacteria cell; multiple types of inactivated bacteria and multiple types of inactivated viruses; and so on).

In an embodiment, the particle-imprinted polymer film can differentiate among inactivated cells even if the inactivated cells have a similar size and shape and/or of similar particle types (e.g., two types of inactivated bacilli). Once the inactivated cells are captured by the particle-imprinted polymer film, the cells can be viewed using a microscope, visually, or the like. Also, the inactivated cells can be removed or released from the particle-imprinted polymer film and further analyzed or studied.

In an embodiment, it is advantageous to use inactivated particles such as inactivated cells (e.g., bacteria). In particular, one advantage of using inactivated cells is that it would eliminate the risk of handling infectious microorganism during both production of the particle imprinted polymer film and during cell sorting. In addition, the inactivated cells will not secrete extracellular matrix materials, which assist the cells to attach to the substrate; therefore the non-specific binding of cells are reduced. Furthermore, the fixed inactivated cells have more rigid surfaces, which enhance recognition efficiency/selectivity. In particular, experimentation shows that separating mycobacteria from other bacteria resulted in a 2.5 fold higher selectivity when inactivated bacteria were used as template and sample, compared with that which was achieved using living bacteria (See Table 1 below).

TABLE 1

Inactivation of Bacteria for Cell-Imprinted Polymer Surfaces Number of bacterial cells captured on PDMS surface that contains imprints of *M. smeg*. PDMS imprinted with untreated *M. smeg* was used in the experiments for capturing untreated bacteria, whereas PDMS imprinted with formaldehyde-inactivated *M. smeg* (4% formalin for 10 min) was used in the experiments for capturing formaldehyde-inactivated bacteria. The standard deviation was calculated from five replicate measurements.

|  | *M. smeg* | *S. aureus* | *E. coli* |
| --- | --- | --- | --- |
| Untreated bacteria | 63 ± 7 | 27 ± 5 | 34 ± 4 |
| Inactivated bacteria | 54 ± 4 | 10 ± 2 | 12 ± 2 |

In an embodiment, the target particles can be inactivated using physical inactivation and chemical inactivation. Inactivation could lead to a change in performance in the selective reincorporation of target (imprinted) cells. Physical inactivation (e.g., heating or UV treatment) terminates the biological activity by damaging the DNA molecules and/or denaturing the proteins. Physical inactivation can effectively eliminate the formation of a thin film during template preparation. The formation of thin film was observed when living bacteria were used for preparing the template, which could weaken the recognition effect as the surface of bacteria will be covered by a uniform thin layer of extracellular matrix material secreted by the template cells. The physical inactivation, therefore, could help to make sure the surfaces of template bacterial cells are exposed to the imprinting polymer.

Chemical inactivation can also prevent the formation of a thin film during template preparation. In addition, chemical inactivation can crosslink the functional groups on cell surface, which helps to better maintain the morphology of cells and the structure on their surface. In this way, the chemical inactivation could generally achieve greater selectivity (versus without treatment). In an embodiment, chemical inactivation can include a combination of formaldehyde and glutaraldehyde (e.g., 4% formaldehyde and 2% glutaraldehyde).

In an embodiment, the particle-imprinted polymer film can be a polymer film. In an embodiment, the polymer can be polydimethylsiloxane (PDMS), polyurethanes, polyimides, polymethyl methacrylate (PMMA), poly(isobutylene) (PIB), polyethylene-co-propylene) (E/Pco), polystyrene-butadiene) (PSB), low density polyethylene (LDPE), polybutadiene cis/trans (PBCT), poly(acrylonitrile-co-butadiene) (PAB), poly(acrylate) (PA), poly(dimethylsiloxane)/poly(divinylbenzene) (PDMS/DVBS), and poly(ethylene glycol)/poly(divinylbenzene), and a combination thereof or containing other additives to enhance non-covalent binding recognition. In addition, initiators, cross-linkers, and the like can be used with the appropriate prepolymer to form the polymer.

In an embodiment, the particle-imprinted polymer film can be a co-polymer film. In an embodiment, the prepolymer can include a copolymer that has a specific affinity to characteristic components (e.g., hydrophobic characteristic) on the surface of the target particle. In an embodiment, the prepolymer can include a copolymer of poly(diallydimethylammonium chloride (PDADMAC) and polydimethylsiloxane (PDMS).

In an embodiment, functional components can be included in the particle-imprinted polymer film to promote binding and/or inhibit nonspecific binding. In an embodiment, the functional components that promote binding show select affinity for characteristic components of the target cells surfaces. In an embodiment, the functional components that promote binding can include: high-charge-density molecules, ligands, and a combination thereof.

In an embodiment, the functional components that inhibit nonspecific binding appear to fill in the areas of the imprinted surface where no cell previously covered it, which enhanced selectivity. In an embodiment, the functional components that inhibit nonspecific binding can include: fluoropolymers, poly(ethylene glycol) (PEG), poly(ethylene glycol) methyl ether methacrylate (PEGMEM), and a combination thereof.

In a particular embodiment, the copolymer presents a specific affinity to hydrophobic components on the surface of mycobacteria. The bacterial template is made to contact with the prepolymer mixture, causing non-covalent binding sites to form between the cell surface and the polymeric substrate via self-assembly. Specifically, the copolymer additive, PDADMAC, tends to aggregate around the mycobacteria cell surface because of their specific affinity to the hydrophobic molecules on the surface of mycobacteria. When the polymer is hardened and the template is removed, a pattern is left behind that is able to preferentially capture the mycobacteria cells when a mixture of cells is flowed over the polymer surface. The imprints on PDMS generated with PDADMAC copolymer additive present a higher preference in capturing mycobacteria, compared with imprints made without the additive. When separating *Mycobacterium smegmatis* from other bacteria, a 2.5 fold increase in selectivity was achieved by adding trace amount of PDADMAC into a PDMS prepolymer for making the cell imprints.

TABLE 2

Enhanced Imprints of Mycobacteria in Polymer Films with a Copolymer Additive Number of bacterial cells captured on PDMS imprints and PDADMAC-doped PDMS imprints. A mixture of *E. coli* and *S. aureus* was used as a sample of other bacteria. The capture test was carried out in closed tubes shaken at 60 rpm for 2 h. The slide was rinsed by distilled water before inspected under a microscope. The standard deviation was calculated from three replicate measurements.

| Bacterium species | PDMS | PDMS-PDADMAC |
| --- | --- | --- |
| *M. smegmatis* | 15 ± 2 | 37 ± 3 |
| Other bacteria | 3 ± 1 | 3 ± 1 |

In an embodiment, different strains of mycobacteria can be separated using embodiments of the present disclosure. In particular, MTB H37Rv can be separated from MTB ΔLprG. Additional details are provided in the Examples.

In an embodiment, the thickness of the particle-imprinted polymer film can be about 1 micron or larger or about 1 to 100 microns. In an embodiment, the indentations can have a depth of about 2 nm or larger or about 2 to 1000 nm, and have a width of about 2 nm to larger or about 2 to 10000 nm. The dimensions can be designed to operate in a desired device or system (e.g., microfluidic device) for the desired particles.

In an embodiment, the particle-imprinted polymer film can have one portion of the particle-imprinted polymer film having a functional additive that anchors to the polymer matrix (e.g., PDMS polymer matrix) during the imprinting process, while another portion has a similar function additive but it does not anchor to the polymer matrix. In an embodiment, the portion with the anchored functional additive may generate a more stable chemical pattern on the resulting surface than those with similar structures but without anchor factors. Addition details are provided in the Examples.

In an embodiment, the particle-imprinted polymer film can be incorporated into microfluidic systems, separation systems (e.g., FACS) as a pre-separator, and the like. In a microfluidic system an inlet flow system and outset flow system can be used to flow samples including cells, reagents, wash reagents, and the like across the particle-imprinted polymer film.

In an embodiment, the particle-imprinted polymer film can be formed by disposing a known particle (e.g., a buffered cell suspension) onto a first substrate, where the particles (e.g., cells) are attached to the first substrate. In an embodiment, the first substrate can include any rigid support such as a glass or quartz or ceramic, or plastic, or metal plate (slide). In an embodiment, the attached cells on the first substrate form a stamp. In an embodiment, a prepolymer is disposed (e.g., spin coated or other equivalent technique) and partially cured on a second substrate. The prepolymer can include monomers and other components that are used to form one of the polymers mentioned herein. In an embodiment, the prepolymer of the polymer can be mixed with a solvent such as hexane, cyclohexane, or the like, prior to disposing the prepolymer on the first substrate. Next the stamp is pressed into the partially cured prepolymer film and then cured. Curing can be accomplished in different means such as by temperature and/or by irradiation. The prepolymer organizes around the cells of the stamp to form indentions that have a shape and size corresponding to the cells and at the molecular level the indentations have non-covalent characteristics that facilitate the capture of the cells. Although not intending to be bound by theory, one of the major forces driving capture of the cells using this technique appears to be non-covalent characteristics of the indentations. As noted above, the indentions preferentially capture at least one target cell when exposed to a sample including the target cells.

After curing, the stamp is removed and then any cell residue is removed (e.g., sonication) to expose the particle-imprinted polymer film. In an embodiment, the particle-imprinted polymer film can be additionally treated to add functionality to, to change functionality of, and/or to remove functionality from, the particle-imprinted polymer film. Modification of the functionality of the particle-imprinted polymer film can be performed to enhance specificity and/or improve efficiency of the capturing of the particles, as described herein. In addition, adjustment of the pH (i.e., higher or lower) and orientation (i.e., parallel to the flow of the sample) of the particle-imprinted polymer film with the flow of sample can enhance efficiency.

An embodiment of the present disclosure includes methods of separating particles. In an embodiment, the particles can include those that can be separated by affinity based method. In an embodiment, the particles are cells such as unicellular organisms such as algae, bacteria, archaea, protists, and/or fungi as well as modified types of these cells. In an embodiment, the cells can include animal (e.g., mammal) or human cells as well as modified types of these cells. In an embodiment, the cells can include stem cells, oocytes, blood cells, cancer cells, and the like, as well as modified types of any of these cells. In an embodiment, the particles can include eggs and modified types of eggs. In addition, in an embodiment the particles can include viruses as well as modified types of these viruses. In an embodiment, the particles can include cell debris. In an embodiment, tuberculosis cells can be captured and additional details are described in the Examples. In particular, particles having a similar density as water and/or no magnetic response can be separated using embodiments of the present disclosure.

Moreover, the cells can be modified prior to imprinting and to sampling. Modified types of the particles can be used to form the particle-imprinted polymer film and can be used to capture modified types of particles in a sample using the particle-imprinted polymer film. In an embodiment, it may be advantageous to inactivate the particles, in certain types of cells for safety purposes of handling. So the cells can be modified and then used to form the particle-imprinted polymer film. Subsequently, target cells can be modified in the same way and captured by the particle-imprinted polymer film.

In an embodiment, the particles can be separated by exposing a particle-imprinted polymer film to a sample that can include one or more types of target particles (e.g., target cell). As noted herein, the indentations preferentially capture the target particles in the sample. Any material in the sample transferred from the stamp can be removed from the particle-imprinted polymer film continuously during the capture process or after an appropriate amount of time. Subsequently, the particle-imprinted polymer film can be inspected (e.g., microscopy and the like) to determine if and how many particles were captured. Additional analysis can be conducted as needed. The captured particles can be removed or released from the particle-imprinted polymer film using washing techniques (e.g., wash with polylysine), sonication, and the like. In addition, residual cell material can be removed using techniques such as sonication and stronger washing techniques. In an embodiment, the cell-imprinted polymer film can be reused for multiple capture and release cycles. In another embodiment, more than one type of cell can be imprinted on the polymer film, either in distinct regions or together (e.g., randomly disposed).

In an embodiment, this process can be repeated for the particles that are separated to increase efficiency and/or separate particles having similar characteristics (e.g., volume). For example, the separated flow can be recirculated through the same channel or can be flowed through a different channel if a device includes two or more channels and means for actuating fluid motion.

In affinity-based particle sorting methods, the sensitivity is also controlled by the chance of particles coming into contact with the surface, which is actually not easy. According to hydrodynamic theory, close to the solid surface there is a boundary layer of several to tens of microns across which the flow rate gradually drops to near zero. The analyte must pass through this boundary layer by diffusion or, by application of some external force field, to contact the solid textured surface. As smaller objects diffuse faster in liquid, this is not a problem for smaller analytes like molecules or even proteins, but could be a significant hurdle for particles, especially those bio-particles whose density are close to the density of water. Sedimentation of bacteria is at a velocity close to 100 nm/s; therefore, it could take minutes for the bacteria to travel across the boundary layer.

To overcome this problem, a structure (e.g., a turntable device) can be used that employs centrifugal force to accelerate the speed of particle-surface contact. In an embodiment, the bulk fluid in the inlet reservoir brings the particles into a very shallow channel, where the particles only have tens of microns to travel before contact with the target surface, and the centrifugal force helps the particles travel through that boundary layer. In this way, running at very low spinning rate (for example, 300 rpm), could effectively force most of the particles to contact the capturing surface, thereby greatly enhancing the capture efficiency, and thus reducing the operation time. In an embodiment, this function can be accomplished by the combination of microfluidic structure and vertical centrifugal force, neither of which could by itself realize this function. In this design, the centrifugal force not only drags the particle toward the channel surface, but also drives the liquid moving through the device. Therefore, multiple channels could operate simultaneously without any pumping system. In addition, as the spinning rate required is very low, the device could be operated with a simple mechanical setup, which might be ideal for onsite application in areas having no electricity.

In an embodiment, the target particles can be separated using a microfluidic device that uses centrifugal force. In an embodiment, the device includes one or more sample holding areas that a sample(s) can be disposed. In an embodiment, the sample hold area can be in fluidic communication with a second area directly or using a channel through one or more inlets. In an embodiment, the second area includes one or more particle-imprinted polymer films as described herein. In an embodiment, the device includes a structure that is used to generate a centrifugal force. In an embodiment, the sample holding area and the second area are disposed on or are part of the structure. In an embodiment, each particle-imprinted polymer film is disposed on a substrate that is in a plane that is at an angle (e.g., 1 to 45 degrees) to the plane of the centrifugal force. In an embodiment, the centrifugal force causes the sample to move from the sample holding area into the second area. In particular, the centrifugal force causes the target particles to contact the particle-imprinted polymer film at a greater rate than if the sample were pressure driven to flow across the particle-imprinted polymer film. In an embodiment, the sample hold area is positioned closer to the center of the structure than the second area so the centrifugal force causes the sample to move from the sample holding area to the second area. In an embodiment, the sample holding area is positioned in the center of the structure and the second area is positioned adjacent the sample holding area in an area offset from the center of the structure.

In a particular embodiment, a microfluidic channel is fabricated over a particle-imprinted polymer film. The channel can be several to tens of micron in height and can be in fluidic communication (e.g., connected) to the sample holding area or reservoir and a second area that includes one or more particle-imprinted polymer films. Each of these components is disposed on a structure that is used to generate a centrifugal force (e.g., a turntable). One or multiple such devices are fixed on the turntable, with a dip or incline angle (e.g., 1 to 45 degrees) with the turntable plane (as seen in FIG. 1.1). A suspension of particles, e.g., bacteria, is added to the sample holding area. In an embodiment, the turntable is rotated at a rate of several hundreds rpm until the liquid moves to the second area (e.g., typically within several minutes). The particles are dragged by the centrifugal force toward the capturing surface when they are brought by the bulk fluid into the shallow channel that includes one or more particle-imprinted polymer films, where they only have several to tens of microns to travel before contact with the target surface. This design realizes rapid affinity-based particle sorting by greatly increasing the rate of particles becoming in contact with the particle-imprinted polymer film. Compared with flowing mycobacteria suspension through the same microchannel structure by liquid pressure, a 20-fold increase of capturing efficiency by cell-imprinted polymer films was obtained with the presented turntable design (as seen in FIG. 1.2). The increase of capturing efficiency is estimated to be even higher if compared with capturing setup without microfluidic design. The data shown in FIG. 1.2 were collected with a turntable speed of 300 rpm. The turntable can be caused to rotate by an electric motor or alternatively, it can also be operated by hand using a crank.

EXAMPLES

Now having described the embodiments of the disclosure, in general, the example describes some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Brief Introduction:

Separation of compounds out of complex mixtures is a key issue that has been solved for small molecules by chromatography. However, general methods for the separation of large bio-particles, such as cells, are still challenging. We demonstrate integration of imprinted polymeric films (IPF) into a microfluidic chip, which preferentially capture cells matching an imprint template, and separate strains of cyanobacteria with 80-90% efficiency, despite a minimal difference in morphology and fluorescence, demonstrating its general nature. It is currently thought that the imprinting process, conducted while the polymer cures, transfers chemical information of the cell's external structure to the substrate. Capture specificity and separation can be further enhanced by orienting the imprints parallel to the flow vector and tuning the pH to a lower range.

Introduction:

Separation is a key issue in many fields and applications, including analytical chemistry, diagnostics, environmental science, and synthesis and purification. In contrast to separations of small molecules, which can be performed reliably via chromatography, cell separations are still challenging. Filter-based and magnetic separations are the methods of choice to handle multiple cells simultaneously; however, they require that cells possess a significant size difference or be magnetically labeled.

Molecularly imprinted polymers are widely used as stationary phases in chromatography, sensors, platforms for drug delivery, as well as artificial enzymes. They are relatively cheap and easy to produce, and the high number of commercially available monomers allows for properties to be tuned for different analytes. However, large bio-particles such as proteins, viruses and entire cells cannot diffuse through a bulk imprinted material. The use of a molecularly imprinted polymer film (IPF) circumvents this problem, but exposure of the particles to the stationary phase is limited to only the surface of the film. Microfluidics offers an attractive solution to this problem, as the surface-to-volume ratio of such architectures is dramatically increased compared to macroscale techniques, diffusion distances are decreased, and the IPF may be integrated with other analytical techniques on the same microdevice. However, IPFs incorporated into microfluidic platforms have, as of yet, only been applied to bio-particles such as proteins and viruses; not cells. A recent review of this topic may be found elsewhere.

IPFs are imprinted with templates of the target cell, forming complexes between the polymer and the analyte via selfassembly. It is theorized that the electrostatic interactions between the polymer and the cell surface continue through the cross-linking process, effectively molding the cell surface's chemical information into the polymer's exposed functional groups. When the cells are removed after the polymer substrate has been cured, they leave behind imprints that can recognize and reincorporate other cells of that template.

We demonstrate here the first use of microfluidic IPF devices for effective and specific cell separation. The effectiveness of this technique may be further enhanced by sequential separations, adjustment of pH, and the use of oriented imprints. The general nature of this technique, essentially matching a template's chemical fingerprint to that of cells in a sample, holds promise for use in a number of fields. In this study, we have performed all separations on strains of *Synechococcus* and *Synechocystis cyanobacteria*, which represent important organisms which arise from exceptionally diverse microenvironments indicating the possible application of this technique toward separation of target organisms from complex samples. We chose two related strains of *Synechococcus* to demonstrate the specificity of this sorting technique. The external layers of these cells are expected to be exceptionally diverse, a feature believed to arise from environmental factors. We believe that the use of microfluidic IPF devices for bacterial sorting is general and can be applied to a wide range of other cell types.

Experimental Details:
Materials:

*Synechococcus* OS-B0 (Syn OS-B0), *Synechococcus elongatus* PCC 7942 (Syn 7942), and *Synechocystis* PCC 6803 (6803) were obtained from the laboratory of Devaki Bhaya in the Department of Plant Biology, Carnegie Institute of Washington. Poly(dimethylsiloxane) (PDMS) was obtained from RS Hughes. A viability test was performed using LIVE/DEAD® BacLight™ Bacterial Viability Kit (Invitrogen) following the protocol given by the vendor. All other chemicals were purchased in highest or analytical grade from Sigma Aldrich or VWR.

Fabrication of Microfluidic Chips:

The microfluidic chips are composed of two parts: a top PDMS layer, containing a simple serpentine microfluidic channel, and an IPF. The serpentine channel (20 mm in height, 100 mm in width, and 61.88 mm in length) was cast into the PDMS via standard soft lithography. The top layer was bonded to the imprinted polymer using PDMS-mortar (10:1 PDMS diluted in four parts toluene spin-coated on glass and pre-cured at 80° C. for 4 min) The fabrication of the imprinted polymers is described below.

Preparation of Template Stamps:

A prerequisite for imprinting with cyanobacteria is a glass stamp with adhered cells. For this work, stamps with cells in a random or defined orientation were used. For randomly oriented cells, 5×5 mm pieces of microscope slides were polished with Kim-wipes (to remove dust or fingerprints) and 40 ml of cell suspension (approximately 3×10 cells mL$^{-1}$) was spread on the surface. After 30 min at 4° C., the cells had settled down on the glass plate and the surplus solvent was removed by spinning the slide at 1500 rpm (1 min) prior to drying. This step is critical to prevent crystallized buffer salts from covering cells and obstructing imprinting.

FIG. 2.1 illustrates how stamps with cells in a defined orientation were produced. A glass plate covered with 0.01% polylysine solution was left at room temperature for 10 min. Surplus solvent was removed on the edges with a Kimwipe, followed by drying. A directional flow was employed to promote cell placement on the surface in a defined orientation. This was achieved by temporarily binding a PDMS layer containing a serpentine channel to the glass plate, via simple electrostatic interaction. Consequently, the binding was not very strong and negative pressure was needed to apply a flow. A pipette tip, serving as reservoir, was connected to the inlet and a syringe was used to suck cell suspension through the chip from the outlet. During that process, the rod-shaped cells were bound to the surface, oriented with the flow vector. 50 μL, which corresponds to approximately 10 cells mL$^{-1}$, was moved through the chip. After removal of the suspension, the PDMS was peeled from the glass plate, which could then be used for imprinting.

Fabrication of Molecularly Imprinted Films:

Optimization of the imprinting protocol was conducted, and is discussed in the Supplementary Information describe below. Briefly, the optimal protocol was determined to be as follows. 2 parts 10:1 (monomer:crosslinker) PDMS was diluted with 1 part cyclohexane and spin-coated onto a microscope slide (30 s at 1500 rpm). Pre-curing at 80° C. for 4 min enhances the viscosity of the prepolymer, preventing the cells from sinking too deeply into the material. Glass stamps with adhered cells were pressed into the prepolymer and the polymer was finally cured at room temperature overnight. Alternatively, curing could also be performed at an elevated temperature. However, it is generally known that molecularly imprinted polymers are more selective if the prepolymer has more time (using a lower temperature) to form high-affinity binding sites.

Cell removal is performed by submerging the IPF in a petri dish filled with distilled water and sonicating for five minutes. The success of the imprinting process can be determined via AFM (FIG. 2.2).

Capture & Separation of *Cyanobacteria*:

A pipette tip was inserted into the chip's inlet, to serve as a reservoir, and filled with cell suspension. The outlet was connected to a syringe and cell suspension was drawn through the channel via negative pressure. After a certain volume (specified respectively for each experiment discussed below) was passed through the device, the channels were scanned on a microscope platform and cells were counted automatically.

An image of an area of the channel was taken using a CCD camera (Mintron MTV-63KR11N) and an inverted microscope (Nikon Eclipse TE2000-U). The brightness of the pixels corresponds to photon counts on a particular area of the CCD chip. A group of pixels exceeding an empirically determined threshold was counted as a particle. A laser beam (Crysta Laser, maximum output power: 495 mW at 633 nm) was expanded to cover an area of approximately 400 μm×400 μm within the separation device, which can be regarded as the detection area. The device was placed on a precisely movable stage (Lstep Märzhäuser) which was controlled remotely. A Labview (National Instruments) program built in-house allowed us to perform a raster scan in order to cover the whole separation area systematically. Additionally, the camera control was synchronized to this scanning movement in such a way that we automatically obtained a composite fluorescence image of the entire separation area. After appropriate calibration for each type of particle, this automated scanning procedure allowed us to achieve a rapid and reliable quantification of the cells caught on the capturing surface.

The chips can be regenerated and the purified cells can be released by washing with an excess of polylysine (0.01%) aqueous solution. The oligopeptide is positively charged and competes with the positive charges on the IPF, causing release of the cells. Three capture and release cycles with Syn OS-B' are shown in FIG. 2.3. Separation capability of the microdevice was first tested and optimized with fluorescent beads and Syn OS-B' (Supplementary Information described below) and a separation efficiency of 90±4% at a flow rate of about 20 mL min$^{-1}$ was achieved.

Results and Discussion:

Cell samples can be significantly enriched on the surface by flushing a cell suspension through the chip. FIG. 2.4 shows an example of Syn OS-B' enrichment on a polylysine-coated surface imprinted with a Syn OS-B' template; saturation occurs after the chip has processed a given volume.

The specificity of IPF capture was evaluated by comparing the capture of the three cell strains across five types of surfaces. It can be seen in FIG. 2.5 that each imprinted film incorporates significantly more cells of its template than non-template cells. This specificity is especially striking between the two strains of *Synechococcus cyanobacteria*, Syn 7942 and Syn OS-B'. Bare PDMS and non-imprinted polylysine-coated glass demonstrate no such specificity.

The separation efficiency that results from this capture specificity was also evaluated. A 1:1 mixture of Syn OS-B' and 6803 (10 cells mL$^{-1}$) was used. The mixture was processed through one of two separate microdevices: one with a 6803-imprinted surface and another with a Syn OS-B'-imprinted surface. Following processing, the resulting suspensions, now depleted in cells matching the imprint template, were analyzed by flow cytometry. The efficacy of sequential separations was examined by processing suspensions through several new chips with the same type of IPF. FIG. 2.6 shows that processing through one device of either IPF type results in a separation efficiency of about 80%, while processing through sequential devices of the same type can improve the efficiency up to about 90%.

FIG. 2.7 shows the sensor response of a surface imprinted with Syn OS-B', and two non-imprinted references: bare PDMS and polylysine-coated glass. The imprinted surface exhibits much greater sensitivity than both non-imprinted references. We believe that this indicates promising potential for microfluidic IPF devices to be used in bacterial detection applications, such as medical diagnostics or characterization of environmental bacterial populations.

Adhesion of cells to imprinted surfaces, and thus the sensitivity and efficiency of capture and separation, can be further enhanced by adjusting the pH of the suspension. Suspensions of Syn OS-B' and Syn 7942 were processed through chips with Syn OS-B'-imprinted IPFs, as well as a chip with a non-imprinted reference (FIG. 2.8). pH was tuned using either KOH, acetic acid or HCl, and no significant difference was observed between the effects of the additives (data not shown). At a sufficiently low value (pH 4), more cells of both types were captured than at pH 7. However, there is exists an optimal value (pH 5) where selectivity greatly enhanced, as more Syn OS-B' cells are captured while 'crosscapture' of Syn 7942 is actually reduced. We believe that this effect is explained by protonation of functional groups, both on the surfaces of the cells and the imprints, leading to a more favorable electrostatic interaction between the two. Notably, viability of cells that are captured and then flushed from the device changes only slightly over the range of this pH (FIG. 2.8, bottom), from the value of 63±4% on a non-imprinted reference at pH 7.

Further enhancement to capture efficiency and sensitivity can be achieved by creating an IPF where the imprints are in a single defined orientation. Imprints oriented parallel to the flow, perpendicular to the flow, and at random were tested against a non-imprinted PDMS reference (FIG. 2.9). Imprints oriented parallel to the flow show an enhanced capturing efficiency compared to imprints oriented perpendicular to the flow or at random, though all imprint directions are still more sensitive than a non-imprinted surface. Additionally, pH adjustment can be used to enhance capture even further.

Conclusions:

We have demonstrated the first use of microfluidic IPF devices for cell capture and separation, as well as the first use of oriented imprints. We have demonstrated that microfluidic IPFs possess a high specificity for template cells, even when a suspension contains species having very similar morphologies that cannot be well-distinguished by size-based methods. When separating different strains of cyanobacteria, separation efficiencies between 80% and 90% were achieved, depending on the number of sequential separations employed. Additionally, we demonstrated that microfluidic IPFs have a dynamic sensor response, indicating their potential use for bacterial detection applications.

The initial achievements in separation efficiency and cell capture were demonstrated to be enhanced via several techniques. In addition to simple additional processing in sequence with the same microfluidic IPF type, separation could also be improved by adjusting the pH to a more acidic value and orienting the imprints parallel to the flow direction. As it is currently thought that molecular imprinting transfers chemical information of a cell's external architecture to the polymer, these methods hold promise as an effective, general method for cell separation that does not require significant differences in morphology or labels (magnetic, fluorescent, or otherwise).

While our work here with cyanobacteria demonstrates this technique has potential for working with bacteria that typically arise from diverse microenvironments, we believe this technique may also have important uses in medical diagnostics, such as detection of one or a mix of suspected agents from blood or urine samples. The power of this technique arises from its general nature, relying purely on the chemical fingerprint of a cell's surface.

REFERENCES, EACH OF WHICH IS
INCORPORATED HEREIN BY REFERENCE

1 B.-H. Chueh, D. Huh, C. R. Kyrtsos, T. Houssin, N. Futai and S. Takayama, Anal. Chem., 2007, 79, 3504.
2 H. Wei, B.-H. Chueh, H. Wu, E. W. Hall, C.-W. Li, R. Schirhagl, J.-M. Li and R. N. Zare, Lab Chip, 2011, 11, 238.
3 R. Schirhagl, I. Fuereder, E. W. Hall, B. C. Medeiros and R. N. Zare, Lab Chip, 2011, 11, 3130.
4 J. A. Davis, D. W. Inglis, K. J. Morton, D. A. Lawrence, L. R. Huang, S. Y. Chou, J. C. Sturm and R. H. Austin, Proc. Natl. Acad. Sci. U.S.A., 2006, 103, 14779.
5 S. Thorslund, O. Klett, F. Nikolajeff, K. Markides and J. Bergquist, Biomed. Microdevices, 2006, 8, 73.
6 G. Wulff and A. Sarhan, Angew. Chem., Int. Ed. Engl., 1972, 11, 34.

7 A. Prieto, S. Schrader, C. Bauer and M. Meoder, Anal. Chim. Acta, 2011, 685, 146.
8 B. Sellergren, B. Ekberg and K. Mosbach, J. Chromatogr., A, 1985, 347, 1.
9 R. Schirhagl, D. Podlipna, P. A. Lieberzeit and F. L. Dickert, Chem. Commun., 2010, 46, 3128.
10 R. Schirhagl, A. Seifner, F. T. Hussain, M. Cichna-Markl, P. A. Lieberzeit and F. L. Dickert, Sens. Lett., 2010, 8, 399.
11 A. Mujahid, A. Afzal, G. Glanzing, A. Leidl, P. A. Lieberzeit and F. L. Dickert, Anal. Chim. Acta, 2010, 675, 53.
12 M. D. Sousa and C. M. Barbosa, Quim. Nova, 2009, 32, 1609.
13 D. R. Kryscio and N. A. Peppas, AIChE J., 2009, 55, 1311.
14 G. Wulff, B.-O. Chong and U. Kolb, Angew. Chem., Int. Ed., 2006, 45, 2955.
15 B. T. S. Bui and K. Haupt, Anal. Bioanal. Chem., 2010, 398, 2481.
16 T. A. Sergeyeva, O. A. Slinchenko, L. A. Gorbach, V. F. Matyushov, O. O. Brovko, S. A. Piletsky, L. M. Sergeeva and G. V. Elska, Anal. Chim. Acta, 2010, 659, 274.
17 S. A. Piletsky and A. P. F. Turner, Electroanalysis, 2002, 14, 317.
18 L. Braco, K. Dabulis and A. M. Klibanov, Proc. Natl. Acad. Sci. U.S.A., 1990, 87, 1274.
19 M. J. Whitcombe, I. Chianella, L. Larcombe, S. A. Piletsky, J. Noble, R. Porter and A. Horgan, Chem. Soc. Rev., 2011, 40, 1547.
20 M. Jenik, R. Schirhagl, C. Schirk, O. Hayden, P. Lieberzeit, D. Blaas, G. Paul and F. L. Dickert, Anal. Chem., 2009, 81, 5320.
21 F. L. Dickert, O. Hayden and K. P. Halikias, Analyst, 2001, 126, 766.
22 P. A. Lieberzeit, A. Findeisen, J. Meahner, R. Samardzic, J. Pitkeanen, O. Anttalainen and F. L. Dickert, Procedia Eng., 2010, 5, 381.
23 N. M. Bergmann and N. A. Peppas, Prog. Polym. Sci., 2008, 33, 271.
24 G. M. Birnbaumer, P. A. Lieberzeit, L. Richter, R. Schirhagl, M. Milnera, F. L. Dickert, A. Bailey and P. Ertl, Lab Chip, 2009, 9, 3549.
25 R. Schirhagl, K. Ren and R. N. Zare, Science China Chemistry, 2012 (in press).
26 J. O'Mahony, B. C. G. Karlsson, B. Mizaikoff and I. A. Nichols, Analyst, 2007, 132, 1161.
27 S. Wei, M. Jakusch and B. Mizaikoff, Anal. Bioanal. Chem., 2007, 389, 423.
28 J. F. Heidelberg, W. C. Nelson, T. Schoenfeld and D. Bhaya, PLoS One, 2008, 4, e4169.
29 E. Hoiczyk and A. Hansel, J. Bacteriol., 2000, 182, 1191.
30 A. M. Rampey, R. J. Umpleby, G. T. Rushton, J. C. Iseman, R. N. Shah and K. D Shimizu, Anal. Chem., 2004, 76, 1123.

Supplementary Information for Example 1:

Chip Fabrication:

The optimal imprinted polymer has as many binding sites as possible, leading to higher sensitivities. In order to achieve this goal, polymerizing conditions were varied. 10:1 PDMS was chosen because it is known to replicate structures on silicon wafers. Furthermore, it is transparent and biocompatible, and thus can easily be used for optical detection with minimal impact on cell viability. The mixture of the prepolymer into cyclohexane was varied from 9-100% PDMS. Each mixture was spin-coated onto microscope slides and three sets of experiments were performed, where the coated microscope slides were pre-cured 0, 4, and 5 minutes before imprinting (only the data for 5 min, which performed the best, is shown). For 0 and 4 min pre-curing times, the polymer was too soft and very few imprints could be found. After imprinting, the stamps were removed and the surfaces were observed under AFM to determine the imprinting density as well as the depth of the imprints. The optimization for 5 min pre-curing is depicted in FIG. 2.10. A 2:1 PDMS:cyclohexane mixture was found to be best and thus was used for all further experiments.

An embodiment of the chip fabrication is shown in FIG. 2.11. The top layer is dipped into pre-cured PDMS mortar. When the top layer is released the mortar sticks to the areas between channels so that the top layer can be bound to the capturing surface.

Adhesion-Based Separation:

In order to initially evaluate the utility of microfluidic molecularly imprinted films, *Synechococus* OS-B' and fluorescent beads were mixed together and then processed through the separation device. FIG. 2.12 shows flow cytometery measurements of the pure components, while FIG. 2.13 shows measurements for suspensions before and after separation.

Example 2

Brief Introduction:

A glass slide covered with bacteria is pressed into another glass slide coated with partially cured polydimethylsiloxane (PDMS). The PDMS is hardened and the cells are removed to create a textured surface whose indentations preferentially capture the same type of bacteria when a mixture of bacteria is flowed over it. Overcoating the cell-imprinted PDMS with methylsilane groups causes the resulting surface to lose much of its ability to preferentially capture the imprinted bacteria, although the shapes of the imprints, measured by atomic force field microscopy, are shown to be hardly affected. We interpret this behavior as strong evidence that chemical recognition plays a dominant role in cell sorting.

Introduction:

The history of what is called "molecular imprinting" seems to be a bit convoluted.[1,2] It seems to have been based on the mistaken idea Pauling[3] put forward to explain how antibodies are made, which involves a protein antibody self-assembling about an antigen template. Pauling suggested to his postdoctoral student Dickey that he prepare substrate-selective adsorbents. Dickey precipitated a mixture of silica gel and the dye methyl orange, which when washed out of the silica gel caused the silica gel to show an increased affinity for the dye template.[4] Many studies followed, but the selectivity was not particularly good and seemed to degrade with time[5] and there was a problem of reproducibility. The next significant advance in molecular imprinting was made in 1972 by Wulff and Sarhan[6] who used synthetic organic polymers to trap, covalently bond with, and imprint molecules. Independently, another important advance was made in 1981 by Arshady and Mosbach[7] who demonstrated a noncovalent bonding approach to create an imprint of the template molecule within the polymer matrix. By the early 1990s the field of molecular imprinting of polymers was rapidly growing.[1,2] Further successes involved the application of polymer imprinting to objects having a larger and more varied surface area, such as viruses, bacteria, and cells.[8,9] In molecular imprinting, the molecules to be imprinted are first allowed to form complex with the polymerizable entities, which are subsequently cured; after removing the template molecules specific recognition sites are left in the polymer, which are complementary in size and shape to the analyte.[1,2] One question that has remained not completely settled is how the recognition works. It seems to be a combination of physical shape selectivity and chemical recognition. This work investigates this question for cells and reaches the conclusion that chemical recognition plays the dominant role when polydimethylsiloxane (PDMS) is used as the polymeric crosslinking network.

One way to learn about what makes the polymer imprinting mechanism selective is to investigate its use to resolve a racemic mixture of enantiomers. In a series of experiments, Wulff and coworkers[1] polymerized a series of similar monomers with various arrangements of the functional groups or with different spatial properties and determined the resolving power for various sugar racemates when the template sugar enantiomer was removed. It was concluded that "the arrangement of the functional groups in the cavity is the decisive factor for the selectivity, while the shape of the cavity is somewhat less important." The approach of Wulff and coworkers involves the creation of covalent bonds between the molecule template and the polymer network, which are subsequently cleaved. Mosbach and coworkers followed a noncovalent approach which was argued to be more versatile.[2] For example, Ramström, Andersson, and Mosbach[10] demonstrated higher selectivity for carboxylic acids by using a judiciously chosen mixture of monomers. Thus, the importance of chemical recognition cannot be denied, but it remains unclear from past studies how chemical recognition compares with physical shape selectivity for larger objects such as viruses, bacteria, and cells. The goal of this study is to settle this matter in the case of cell-imprinted PDMS, which may be taken as typical of other polymeric networks.

In our experiment, bacteria were selected to be representative of the two Gram-staining groups; in each group, two species similar in shape and size were included. Among them, the two Gram-positive coccus, *Staphylococcus epidermidis* (*S. epidermidis*) and *Staphylococcus aureus* (*S. aureus*) are grape-like in shape with diameters of ~800 nm, whereas the Gram-negative *bacillus, Escherichia coli* (*E. coli*) and *Klebsiella pneumoniae* (*K. pneumoniae*) are rod-shaped, ~2.0 μm long and ~0.5 μm in diameter.[11]

FIG. 3.1 presents the process flow of the experiment we carried out. We prepared a cell-imprinted polymer (CIP) using a surface imprinting method described previously.[8] Buffered cell suspensions of each type of bacteria were spread respectively on glass slides and kept at 4° C. for 1 h. The buffer was then removed by spinning at 2000 rpm to avoid salt crystal formation, leaving the attached cells on the glass substrate, which was then used as the template stamp. We pressed the stamp into a partially cured PDMS membrane and let the polymer cure at 37° C. for 8 h, followed by 80° C. for 1 h. The PDMS kit we used contains a mixture of vinyl terminated PDMS oligomers, crosslinkers of polysiloxanes with vinyl and hydrogen groups, and residual ingredients including octamethylcyclotetrasiloxane, benzene, toluene, ethylbenzene, etc.[12] During the curing under mild temperature, these precursors formed complexes with the cell surface to reach their lowest energy, and the resulting arrangement of the polymer networks was fixed after the curing at 80° C. After that, we peeled off the stamp and removed possible cell residue on the PDMS by sonication. Using fluorescently labeled template cells we verified that no residue remained on the CIP surface. The success of this removal procedure can mainly be attributed to the inertness of the PDMS surface.

To compare CIPs with and without chemical recognition, we modified some of the CIP microfluidic chips with different silanes. Silanization was carried out in a desiccator immediately after $O_2$ plasma treatment. The vapor of different silanes will link to the hydroxyl groups generated on the PDMS by $O_2$ plasma, forming a uniform monolayer of desired groups on the PDMS surface.[13] We found that the silanization could produce surfaces with varying degrees of hydrophobicity and non-specific cell affinity (Table 2.1). Among the silanes (shown in FIG. 3.2B) investigated methyltrichlorosilane produced a surface most closely resembling unmodified PDMS (see FIG. 3.2), and we chose to use this silane in all subsequent experiments.

The morphology of the cavities on this surface are essentially preserved, as the coating thickness is calculated to be on the order of 1 nm. This assertion was verified using atomic force field microscopy (AFM), as shown in FIG. 3.3. Therefore, we believe the modification process using methyltrichlorosilane achieved our goal of removing chemical recognition while maintaining the physical size of the imprints.

We compared the recognition performance of the CIPs before and after silanization (see Table 2.2). Two groups of bacteria were tested as representatives of Gram-positive and Gram-negative bacteria. In each group, two species similar in shape and size were included for testing. The cell capturing experiment was carried out in microfluidic channels. We covered the CIP surface with an array of 30-μm-deep microchannels, which assist the cells in the suspension to make better contact with the CIP surface. The cell suspensions were flowed over the imprints. For each test, we injected a 50 μL cell suspension ($OD_{600}$=0.2) at a flow velocity of ~0.2 mm/s, then rinsed the channel with 50 μL PBS at the same flow rate to avoid random settling of suspended cells on the CIP surface. For visualization, the cells were stained with CellTracker Orange, a fluorescent dye that labels the cell's interior while leaving the cell membrane unaffected[14]. Then, the imprinted surfaces were inspected under a confocal microscope.

FIG. 3.4A shows the selectivity achieved for the unmodified CIPs. We find that the selectivity between the Gram-positive and Gram-negative groups is stronger than the selectivity between the cells in a same group. The two Gram-positive species used are sphere-shaped, whereas the two Gram-negative species are rod-shaped. In addition, some selectivity was also observed between the closely related species in the same Gram groups. However, after silanization (FIG. 3.4B), both the intergroup and the intragroup selectivities are significantly decreased (see Table 2.2). As discussed above, silanization would hardly affect the surface morphology, but it does convert the chemical properties of the surface to be like native PDMS. We believe that FIG. 3.4 presents strong evidence that not only is chemical recognition important but it represents the dominant mechanism for cell selectivity. Nevertheless, as evidenced by the weak intergroup selectivity remaining after silanization, we also believe that physical shape selection is occurring, but to a minor extent. Examination of Table 2.2 shows that CIPs made with one type of bacteria template is able to select the same bacteria in a mixture with a selectivity that is about a factor of two greater than for other bacteria. But silanization of the CIP surface reduces this selectivity to almost no preferential selection. Although it may take more than one sorting cycle to capture and release a nearly pure bacterial strain, the dominant role of chemical recognition seems clearly established by this study.

Experimental:

Materials:

*Escherichia coli* (ATCC 25922), *Klebsiella pneumoniae* (ATCC 33495), *Staphylococcus aureus* (ATCC 29213) and *Staphylococcus epidermidis* (ATCC 12228) were obtained from Niaz Banaei's group in Medical Center, School of Medicine, Stanford University. PDMS was obtained from RS Hughes. CellTracker Orange were purchased from Invitrogen and used following the protocol given by the vendor. All other chemicals were purchased in highest or analytical grade from Sigma Aldrich or VWR.

Cell Handling:

All cell strains were cultured on LB agar plate at 37° C. in an incubator. Before experiment, fresh culture was harvested and rinsed using PBS by centrifuging at 1200 G and 4° C. $OD_{600}$ was used to measure the cell density in a suspension. For visualization, we stained the cells with CellTracker Orange, following the protocol suggested by the vendor.

Template Preparation:

10 µL cell suspension (approximately $10^9$ cells/mL) was spread on the surface of microscope slides and kept at 4° C. for 1 h. After the cells settled down onto the glass surface, the surplus solvent was removed by spinning the slide at 2000 rpm for 1 min.

Stamp Fabrication:

Optimization of the imprinting protocol was conducted and discussed in our previous work. Briefly, we diluted a PDMS curing mixture (monomer: crosslinker=10:1) using cyclohexane to a volume ratio of 2:1, and spin-coated this solution onto a microscope slide (30 at 1500 rpm). After pre-curing the PDMS at 80° C. for 4 min, we pressed the template stamp into the prepolymer and kept the stack at 37° C. for 8 h, followed by 80° C. for 1 h. After that, we peeled the template slide and cleaned the imprinted polymer film by submerging it in a petri dish filled with distilled water and sonicating for 5 min.

Surface Silanization:

The imprinted PDMS slides were treated with a plasma cleaner (Harrick PDC-32G) using 18-W coil power for 10 s, at an air pressure of 200 mTorr. After that, the slides were immediately put into a desiccator, with a test tube containing 10 µL silane in it, and sealed for 3 h. Finally, the slides were cleaned by sonicating in water for 1 min. The substrates were then inspected with a scanning probe microscope (XE-70, Park Systems) using non-contact AFM mode.

Cell Sorting:

PDMS chips containing an array of microchannels were fabricated via standard soft lithography. Each channel was 30-1 µm in height and 100-1 µm in width. The total volume of the channels was about 1 µL. The chip was reversibly bonded to the imprinted substrate by the adhesion between PDMS surfaces without heating or plasma treating process. A pipette tip was inserted into the inlet of the channel as a reservoir, and was filled with cell suspension. A syringe was connected to the outlet of the channel, to draw the cell suspension through the channel via negative pressure. For each test, 50 µL cell suspension ($OD_{600}$=0.2) was infused at a flow velocity of 0.2 mm/s, then 50 µL PBS was used to rinse the channel at the same flow rate. After that, the imprinted area of the chip was inspected under a confocal microscope (TCS SP2, Leica).

TABLE 2.1

Hydrophobicity and non-specific affinity of native and silanized PDMS surfaces. Advancing contact angle of water and non-specific cell adhesion test results of native PDMS and PDMS modified using methyltrichlorosilane, aminophenyltrimethoxysilane, and (tridecafluoro-1,1,2,2-tetrahydrooctyl)-1-trichlorosilane, which introduced alkylsilane, anilinesilane, and fluorosilane groups, respectively. Non-specific affinity to cells was measured with the microfluidic method similar to cell sorting experiment, using 20-µL injections.

| Substrate | Advancing water contact angle | Captured cell numbers/mm |
|---|---|---|
| Native PDMS | 104 ± 1 | 3500 ± 200 |
| Alkylsilane group modified PDMS | 105 ± 1 | 2400 ± 400 |
| Anilinesilane group modified PDMS | 42 ± 2 | 61000 ± 700 |
| Fluorosilane group modified PDMS | 107 ± 1 | 400 ± 100 |

TABLE 2.2

Selectivity of capturing templated bacteria with the cell-imprinted surfaces before and after silanization. The calculation is based on the ratio of numbers of bacteria captured on their imprints to the average number captured on the imprints of the other bacteria.

| Bacteria | Ratio of template imprinted to average of other imprinted | |
|---|---|---|
| | unmodified | modified |
| *E. coli* | 1.8 ± 0.5 | 1.1 ± 0.1 |
| *K. pneumoniae* | 1.8 ± 0.4 | 1.3 ± 0.1 |
| *S. epidermidis* | 2.0 ± 0.3 | 1.3 ± 0.3 |
| *S. aureus* | 2.0 ± 0.4 | 1.2 ± 0.2 |

REFERENCES, EACH OF WHICH IS INCORPORATED HEREIN BY REFERENCE

1. Wulff, G. Molecular Imprinting in Cross-Linked Materials with the Aid of Molecular Templates—A Way towards Artificial Antibodies. *Angew. Chem. Int. Ed.* 1995, 34, 1812-1832.
2. Mosbach, K.; Ramström, O. The Emerging Technique for Molecular Imprinting and Its Future Impact on Biotechnology. *Nature Biotech.* 1996, 14, 163-170.
3. Pauling, L. A Theory of the Structure and Process of Formation of Antibodies. *J. Am. Chem. Soc.* 1940, 62, 2643-2657.
4. Dickey, F. H. The Preparation of Specific Adsorbents. *Proc. Nat. Acad. Sci. USA.* 1949, 35, 227-229.
5. Bernhard, S. A. The Preparation of Specific Adsorbants. *J. Am. Chem. Soc.* 1952, 74, 4946-4947.
6. Wulff, G.; Sarhan, A. The Use of Polymers with Enzyme-Analogous Structures for the Resolution of Racemates. *Angew. Chem. Int. Ed.* 1972, 11, 341-346.
7. Arshady, R.; Mosbach, K. Synthesis of Substrate-selective Polymers by Host-Guest Polymerization. *Makromol. Chem.* 1981, 182, 687-692.
8. Schirhagl, R.; Hall, E. W.; Fuereder, I.; Zare, R. N. Separation of Bacteria with Imprinted Polymeric Films. *Analyst,* 2012, 137, 1495-1499.
9. Schirhagl, R.; Ren, K. N.; Zare, R. N. Surface-Imprinted Polymers in Microfluidic Devices. *Science China Chem.* 2012, 55, 1-15.
10. Ramström, O.; Andersson, L. I.; Mosbach, K. Recognition Sites Incorporating Both Pyridinyl and Carboxy Functionalities Prepared by Molecular Imprinting. *J. Org. Chem.* 1993, 58, 7562-7564.

11. Madigan, M. T.; Martinko, J. M. Brock Biology of Microorganisms, 11th ed. Unit 1. *Upper Saddle River, N.J.: Pearson Prentice Hall*, 2006.
12. Material Safety Data Sheet, RTV615 silicone potting compound, Momentive performance material, 2008-2011.
13. Ferguson, G. S.; Chaudhury, M. K.; Biebuyck, H. A.; Whitesides, G. M. Monolayers on Disordered Substrates: Self-Assembly of Alkyltrichlorosilanes on Surface-Modified Polyethylene and Poly(dimethylsiloxane), *Macromolecules* 1993, 26, 5870-5875.
14. Doerrler, W. T. Lipid Trafficking to the Outer Membrane of Gram-Negative Bacteria. *Mol. Microbiol.* 2006, 60, 542-552.

Example 3

To evaluate the improved performance of our method in identification of bacterial strains we employed two closely related *Mycobacterium* strains, MTB H37Rv and MTB ΔLprG. MTB ΔLprG is a strain obtained by knocking out the genetic information for producing a transmembrane protein, LprG, from the virulent strain of MTB H37Rv. These two strains cannot be successfully differentiated by microscopy methods, but have been found showing markedly different virulence (FIG. 4.1). As LprG is recognized as an anchor factor for cell capsule layer lipoglycan components (LAM, PIM, etc), we suspect that there would be a difference between the two bacterial strains, which may lead to recognition effect through cell-imprinting. We carried out experiment on differentiating the two strains. In the experiment, we compared the performance of different imprinting formulas. In brief, it was rather difficult for a native PDMS polymer to differentiate the two stains, while the PDMS doped with PDADMAC showed a slightly better recognition effect. Among the three strategies tested, the PDMS doped with PEGMEM, based on our new doping strategy involving negative mode (inhibit specific binding), achieved the best recognition effect, as shown in FIG. 4.1. We believe this is evidence that the stains, MTB H37Rv and MTB ΔLprG, have different surface chemistry, which allows them to be differentiated by cell imprinting.

FIG. 4.2 illustrates the numbers of cells captured on cell-imprinted area of polymer surfaces. Suspensions of 4% formaldehyde fixed MTB H37Rv and MTB ΔLprG, respectively, were passed over surfaces containing the imprints of the two stains. The surfaces were prepared with (A) PDMS, (B) PDMS doped with 0.1% PDADMAC and (C) PDMS doped with 0.5% PEGMEM.

Example 4

In an embodiment, the particle-imprinted polymer film can have on one portion of the particle-imprinted polymer film a functional additive that anchors to the polymer matrix (e.g., PDMS polymer matrix) during the imprinting process, while another portion has a similar function additive that does not anchor to the polymer matrix. In an embodiment, the portion with the anchored function additive may generate a more stable chemical pattern on the resulting surface than those with similar structures but without anchor factors.

FIG. 5.1 illustrates an embodiment of the particle-imprinted polymer film where one portion is hydrophobic and the other portion is hydrophilic. Table 5.1 illustrates the contact angle of the two portions.

TABLE 4.1

Advancing water contact angle measured over time, on imprinted PDMS doped with 0.5% free PEG or 0.5% anchored PEGMEM.

| Film formula | 1 h after imprinting | | 2 days after imprinting | |
|---|---|---|---|---|
| | Imprinted with native PS | Imprinted with treated PS | Imprinted with native PS | Imprinted with treated PS |
| 0.5% PEG doped | 102 ± 1 | 100 ± 1 | 102 ± 1 | 102 ± 1 |
| 0.5% PEGMEM doped | 103 ± 1 | 85 ± 2 | 103 ± 1 | 85 ± 2 |

Example 5

FIG. 6.1 illustrates examples of cell capturing result on cell imprints with low occupancy of the surface, prepared with native and PEGMEM-doped PDMS. On average, a 2-fold reduction of non-specific binding on non-imprinted surface was observed. The bacteria used in the test were MTB H37 Rv, stained for fluorescence imaging. In the images, bacteria captured in cavity of imprints are highlighted with green circles, while those on non-imprinted area are highlighted with red circles.

Example 6

The role of inactivation in the imprinting and reincorporation processes has been investigated. Inactivation methods could be divided into two categories, which lead to different performance in the selective reincorporation of target (imprinted) cells. Physical inactivation, e.g., heating or UV treatment, terminate the biological activity by damaging the DNA molecules and/or denaturing the proteins; we found that physical inactivation methods can effectively eliminate the formation of a thin film during template preparation. The formation of thin film was observed when living bacteria were used for preparing the template, which could weaken the recognition effect as the surface of bacteria will be covered by a uniform thin layer of extracellular matrix material secreted by the template cells (see FIG. 7.1). The physical inactivation, therefore, could help to make sure the surfaces of template bacterial cells are exposed to the imprinting polymer.

The other category employs chemicals, particularly those fixatives, to inactivate the cells. The chemical inactivation methods also prevent the formation of thin film during template preparation; in addition, they crosslink the functional groups on cell surface, which help to better maintain the morphology of cells and the structure on their surface. In this way, the chemical inactivation could generally achieve greater selectivity (versus without treatment) (see FIG. 7.2). In particular, we suggest a combination of 4% formaldehyde and 2% glutaraldehyde as the inactivation reagent for cell imprinting (FIG. 7.3). This formula worked better than other chemicals we tested, including bleach, hydrogen peroxide, methanol, ethanol and other concentrations of aldehydes.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the measurement technique and the type of numerical value. In addition, the phrase "about to 'y'" includes "about to about 'y'".

Many variations and modifications may be made to the above-described embodiments. All such modifications and variations are intended to be included herein within the scope of this disclosure and protected by the following claims.

At least the following is claimed:

1. A particle-imprinted polymer film comprising: a single layer polymer film having indentations that have non-covalent chemical binding characteristics that preferentially capture at least one type of target particle via a direct non-covalent interaction with the at least one type of target particle, wherein the polymer film comprises a copolymer that includes polydimethylsiloxane (PDMS), wherein the polymer film is made from a prepolymer that includes a copolymer that has a specific affinity to characteristic components on the surface of an inactivated target particle, and wherein the copolymer is poly(diallydimethylammonium chloride) (PDADMAC) and PDMS.

2. A microfluidic device for separating target particles, comprising:
   a sample holding area;
   a second area including one or more particle-imprinted polymer films having a single layer polymer film having indentations that have non-covalent chemical binding characteristics that preferentially capture at least one type of target particle, wherein second area is in fluidic communication with the sample holding area via one or more inlets; and
   a structure that is used to generate a centrifugal force, wherein the sample holding area and the second area are disposed on or are part of the structure, wherein each single layer polymer film is disposed on a substrate that is in a plane that is at an angle to the plane of the centrifugal force, wherein the centrifugal force is capable of causing a sample to move from the sample holding area into the second area.

3. The microfluidic device of claim 2, wherein the centrifugal force is capable of causing the target particles to contact the single layer polymer film at a greater rate than if the sample were pressure driven to flow across the single layer polymer film.

4. The microfluidic device of claim 2, wherein the sample holding area is positioned in the center of the structure and the second area is positioned adjacent the sample holding area in an area offset from the center of the structure.

5. The microfluidic device of claim 2, wherein the target particles are selected from the group consisting of: active target particles, inactivated target particles, and a combination thereof.

* * * * *